(12) United States Patent
Osslund et al.

(10) Patent No.: US 7,276,477 B2
(45) Date of Patent: Oct. 2, 2007

(54) CRYSTALS OF ETANERCEPT AND METHODS OF MAKING THEREOF

(75) Inventors: Timothy D. Osslund, Camarillo, CA (US); Christi L. Clogston, Newbury Park, CA (US); Shon Lee Crampton, Los Angeles, CA (US); Randal B. Bass, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 112 days.

(21) Appl. No.: 10/901,735

(22) Filed: Jul. 29, 2004

(65) Prior Publication Data

US 2005/0032183 A1 Feb. 10, 2005

Related U.S. Application Data

(60) Provisional application No. 60/491,827, filed on Aug. 1, 2003.

(51) Int. Cl.
*A61K 38/00* (2006.01)
*G01N 38/00* (2006.01)

(52) U.S. Cl. ............................ 514/12; 436/4
(58) Field of Classification Search .................. 514/12; 436/4

See application file for complete search history.

(56) References Cited

U.S. PATENT DOCUMENTS 5,945,397 A * 8/1999 Smith et al. .................... 514/2

OTHER PUBLICATIONS

Drenth, "Principles of Protein X-Ray Crystallography", 2nd Edition, 1999 Springer-Verlag New York Inc., Chapter 1, p. 1-21.*

Giege et al. Crystallogenesis of Biological Macromolecules: Facts and Perspectives, Acta Cryst. D., 1994, D50:339-350.*

Cudney, Protein Crystallization and Dumb Luck, Rigaku Journal, 1999, 16(1):1-7.*

"ENBREL For Subcutaneous Injection" information pamphelet available from the United States FDA at http://www.fda.gov/medwatch/safety/2005/jul_PI/Enbrel_PI.pdf.*

Goffe, B. and J.C. Cather, Etanercept: An Overview, *J. Am. Acad. Dematol.* 49:S105-11 (2003).

Jen, A. and H.P. Merkle, "Diamonds in the Rough: Protein Crystals from a Formulation Perspective," *Pharm. Res.* 18(11):1483-1488 (2001).

Park, Y.C. et al., "Structural basis for self-association and receptor recognition of human TRAF2," *Nature* 398:533-538 (1999).

Scallon, B. et al., "Binding and Functional Comparisons of Two Types of Tumor Necrosis Factor Antagonists," *J. Pharmacol. Exp. Ther.* 301(2):418-426 (2002).

Yang, M.X. et al., "Crystalline monoclonal antibodies for subcutaneous delivery," *Proc. Natl. Acad. Sci. USA* 100(12):6934-6939 (2003).

International Search Report, PCT/US2004/024738,mailed Jan. 7, 2005.

* cited by examiner

*Primary Examiner*—Kathleen Kerr Bragdon
*Assistant Examiner*—Suzanne M. Noakes
(74) *Attorney, Agent, or Firm*—Kathleen Fowler; Suzanne Sprunger

(57) ABSTRACT

The present invention relates to crystalline etanercept and to methods of making crystalline etanercept; to pharmaceutical compositions comprising crystalline etanercept; and to therapeutic uses of such compositions.

29 Claims, 1 Drawing Sheet
(1 of 1 Drawing Sheet(s) Filed in Color)

SEQUENCE LISTING

<160> NUMBER OF SEQ ID NOS: 4

<210> SEQ ID NO 1
<211> LENGTH: 461
<212> TYPE: PRT
<213> ORGANISM: Homo sapiens

<400> SEQUENCE: 1

```
Met Ala Pro Val Ala Val Trp Ala Ala Leu Ala Val Gly Leu Glu Leu
1               5                   10                  15

Trp Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240
```

```
Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
                275                 280                 285

Lys Lys Pro Leu Cys Leu Gln Arg Glu Ala Lys Val Pro His Leu Pro
290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
                340                 345                 350

Val Glu Ala Ser Gly Ala Gly Glu Ala Arg Ala Ser Thr Gly Ser Ser
                355                 360                 365

Asp Ser Ser Pro Gly Gly His Gly Thr Gln Val Asn Val Thr Cys Ile
            370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
                420                 425                 430

Gln Leu Glu Thr Pro Glu Thr Leu Leu Gly Ser Thr Glu Glu Lys Pro
                435                 440                 445

Leu Pro Leu Gly Val Pro Asp Ala Gly Met Lys Pro Ser
            450                 455                 460

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 467
<212> TYPE: PRT
<213> ORGANISM: Artificial Sequence
<220> FEATURE:
<223> OTHER INFORMATION: Fusion polypeptide

<400> SEQUENCE: 4

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
                145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
        180                 185                 190

His Leu Pro Gln Pro Val Ser Thr Arg Ser Gln His Thr Gln Pro Thr
    195                 200                 205
```

-continued

```
Pro Glu Pro Ser Thr Ala Pro Ser Thr Ser Phe Leu Leu Pro Met Gly
    210                 215                 220
Pro Ser Pro Pro Ala Glu Gly Ser Thr Gly Asp Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465
```

CRYSTALS OF ETANERCEPT AND METHODS OF MAKING THEREOF

This application claims the benefit under 35 C.F.R 119(e) of U.S. provisional application Ser. No. 60/491,827, filed Aug. 1, 2003, which is incorporated by reference in its entirety herein.

BACKGROUND OF THE INVENTION

Many therapeutic molecules are polypeptides, some of which are prone to denaturation, degradation, and/or aggregation. Aggregation of polypeptides is undesirable as it may result in immunogenicity (Cleland et al., 1993, *Crit Rev Therapeutic Drug Carrier Systems*, 10: 307-377; and Robbins et al., 1987, *Diabetes*, 36: 838-845). Polypeptides are also subject to catalysis or conversion into inactive forms by the natural biological processes of the organisms to which they are administered. Further, therapeutic polypeptides may be produced as a heterogeneous mixture of forms, varying in the extent of glycosylation or in other aspects of their three-dimensional conformation.

Crystallization of therapeutic polypeptides provides an advantage in producing a stable and homogenous formulation of such polypeptides. Certain advantages of crystals include greater ease of handling of the therapeutic compound in preparing pharmaceutical products; reduced degradation, denaturation and/or aggregation; the potential for creating a sustained release form of the therapeutic polypeptide to reduce the frequency of dosing; and the ability to use crystalline therapeutic polypeptides to form a pharmaceutical composition having a very high concentration of the therapeutic polypeptide. In addition, crystallization methods can produce a more homogenous population of polypeptides in the formulation, because only the addition of similarly configured polypeptide molecules will add to sustained growth of the crystal—when a limiting amount of polypeptides of variant structure have been incorporated into the crystal lattice, the resulting structural weaknesses in the crystal will prevent its further growth. Since incorporation into a crystalline form can ensure that a greater percentage of the polypeptides will be in an active form, administration of a smaller amount of the crystalline therapeutic peptides can produce a therapeutic effect equivalent to administration of a greater amount of a more heterogeneous polypeptide formulation.

Therefore, there is a need for crystalline formulations of therapeutic polypeptides.

SUMMARY OF THE INVENTION

The present invention provides crystalline forms of TNFR2 polypeptides, including crystalline TNFR2:Fc polypeptides and crystalline etanercept. One embodiment of the invention is a crystal of etanercept; in certain embodiments the etanercept crystal is in the form of a rod, and/or has a maximum length of between 0.5 millimeters and 1.5 millimeters or between 0.05 millimeters and 0.3 millimeters.

Also provided by the invention are methods of making crystals of TNFR2 polypeptides such as an TNFR2-Ig fusion polypeptide or etanercept. In certain embodiments, the TNFR2 polypeptides are monomers; in additional embodiments, the TNFR2 polypeptides are multimers such as dimers, trimers, or oligomers. In further embodiments, the TNFR2 polypeptide shares at least 90% amino acid identity across the length of amino acids 39 through 162 of SEQ ID NO:1.

The present invention also relates to the use of the disclosed crystalline TNFR2 polypeptides, such as crystalline TNFR2:Fc polypeptides or crystalline etanercept, in the manufacture of a medicament for the prevention or therapeutic treatment of each medical disorder disclosed herein.

BRIEF DESCRIPTION OF THE DRAWINGS

The patent or application file contains at least one drawing executed in color. Copies of this patent or patent publication with color drawing(s) will be provided by the Patent Office upon request and payment of the necessary fee.

DETAILED DESCRIPTION OF THE INVENTION

Figure 1:
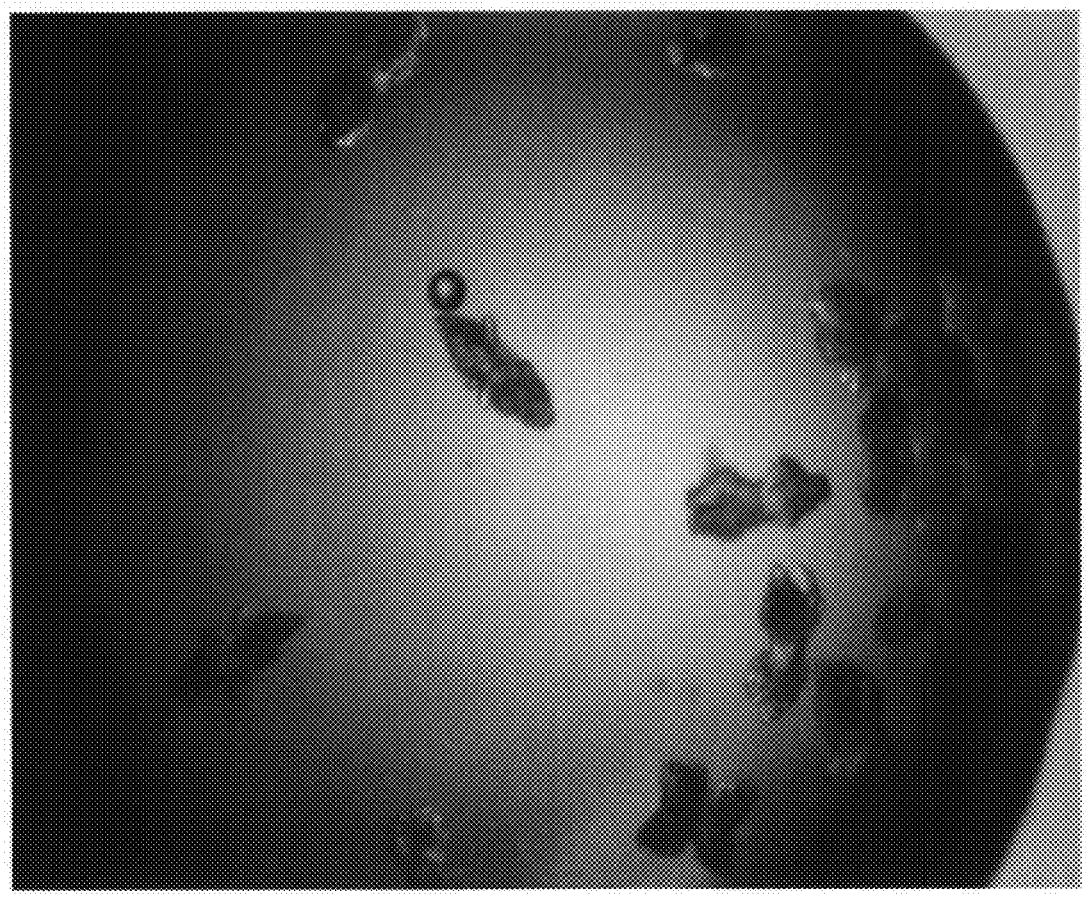
FIG. 1 is a photograph of etanercept crystals formed from a polypeptide solution containing 50.96 mg of etanercept per milliliter, as described further in Example 1 below. The crystallization reservoir buffer was 0.1M HEPES pH 7.0, 30% PEG 6000, 0.7M lithium chloride; after seven days at ambient room temperature the crystals were harvested manually, extensively washed in the above reservoir buffer, and the photograph was taken. Crystals from this group were submitted for N-terminal amino acid sequence analysis.

The invention is directed to TNFR2 polypeptides in crystalline form, and to methods for making and using such crystalline TNFR2 polypeptides. These polypeptide crystals are advantageous in that crystalline polypeptides can be stored for longer periods and can exhibit greater physical stability and retention of biological activity, under a wider range of storage and handling conditions, than polypeptides not in crystalline form.

Definitions

"Polypeptide" is defined herein as natural, synthetic, and recombinant proteins or peptides generally having more than 10 amino acids. A "polypeptide linker" can be a polypeptide formed by a series of amino acids as short as one amino acid in length.

"Isolated", as used herein, refers to a polypeptide or other molecule that has been removed from the environment in which it naturally occurs.

"Substantially purified", as used herein, refers to a polypeptide that is substantially free of other polypeptides present in the environment in which it naturally occurs or in which it was produced; a preparation of a polypeptide that has been substantially purified contains at least 90% by weight (or at least 95%, at least 98%, or at least 99% by weight) of that polypeptide, wherein the weight of the polypeptide includes any carbohydrate, lipid, or other residues covalently attached to the polypeptide. A substantially purified polypeptide preparation may contain variation among polypeptide molecules within the preparation, with respect to extent and type of glycosylation or other post-translation modification, or with respect to conformation or extent of multimerization.

"Purified polypeptide", as used herein, refers to an essentially homogenous polypeptide preparation; however, an essentially homogenous polypeptide preparation may contain variation among polypeptide molecules within the preparation, with respect to extent and type of glycosylation or other post-translation modification, or with respect to conformation or extent of multimerization.

"Full-length" polypeptides are those having the complete primary amino acid sequence of the polypeptide as initially translated; for example, the full-length form of the human TNFR2 is shown as SEQ ID NO:1. The "mature form" of a polypeptide refers to a polypeptide that has undergone post-translational processing steps such as cleavage of the signal sequence or proteolytic cleavage to remove a pro-domain. Multiple mature forms of a particular full-length polypeptide may be produced, for example by cleavage of the signal sequence at multiple sites, or by differential regulation of proteases that cleave the polypeptide. The mature form(s) of such polypeptide can be obtained by expression, in a suitable mammalian cell or other host cell, of a nucleic acid molecule that encodes the full-length polypeptide. The sequence of the mature form of the polypeptide may also be determinable from the amino acid sequence of the full-length form, through identification of signal sequences or protease cleavage sites. In certain embodiments, the mature form of the human TNFR2 polypeptide has an N-terminal amino acid residue selected from the group consisting of amino acids 23, 27, and 28 of SEQ ID NO:1, or an N-terminal amino acid selected from the group consisting of each amino acid between amino acid 1 and amino acid 39 of SEQ ID NO:1.

The "percent identity" of two amino sequences can be determined by visual inspection and mathematical calculation, and the comparison can also be done by comparing sequence information using a computer program. The first step in determining percent identity is aligning the amino acid sequences to so as to maximize overlap and identities, while minimizing gaps in the alignment. The second step in determining percent identity is calculation of the number of identities between the aligned sequences, divided by the total number of amino acids in the alignment. When determining the percent identity that an amino acid sequence has "across the length of" a target amino acid sequence, the length of the target amino acid sequence is the minimum value for the number of total bases in the alignment. For example, when determining the percent identity of a first amino acid sequence of 50 amino acids "across the length of" a second amino acid sequence of amino acids 1 through 100 of SEQ ID NO:X, if the first amino acid sequence is identical to amino acids 1 through 50 of SEQ ID NO:X, the percent identity would be 50%: 50 amino acid identities divided by the total length of the alignment (100 amino acids). An exemplary computer program for aligning amino acid sequences and computing percent identity is the BLASTP program available for use via the National Library of Medicine website ncbi.nlm.nih.gov/gorf/wblast2.cgi, or the UW-BLAST 2.0 algorithm. Standard default parameter settings for UW-BLAST 2.0 are described at the following Internet site: sapiens.wustl.edu/blast/blast/README.html. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, Analysis of compositionally biased regions in sequence databases, *Methods Enzymol.* 266: 554-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); E-score threshold values are 0.5, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100. Other programs used by those skilled in the art of sequence comparison can also be used to align amino acid sequences, such as, the Genetics Computer Group (GCG; Madison, Wis.) Wisconsin package version 10.0 program, 'GAP' (Devereux et al., 1984, *Nucl. Acids Res.* 12: 387). The default parameters for the 'GAP' program include: (1) The GCG implementation of a unary comparison matrix (containing a value of 1 for identities and 0 for non-identities) for nucleotides, and the weighted amino acid comparison matrix of Gribskov and Burgess, *Nucl. Acids Res.* 14:6745, 1986, as described by Schwartz and Dayhoff, eds., *Atlas of Polypeptide Sequence and Structure*, National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps.

"Soluble forms" of TNFR2 polypeptides of the invention comprise certain fragments or domains of these polypeptides. Soluble polypeptides are polypeptides that are capable of being secreted from the cells in which they are expressed. A secreted soluble polypeptide can be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. The use of soluble forms of cytokine polypeptides of the invention is advantageous for many applications. Purification of the polypeptides from recombinant host cells is facilitated, since the soluble polypeptides are secreted from the cells. Moreover, soluble polypeptides are generally more suitable than membrane-bound forms for parenteral administration and for many enzymatic procedures. In certain embodiments of the invention, mature soluble forms of TNFR2 polypeptides do not contain a transmembrane or membrane-anchoring domain such as amino acids 258 through 87 of SEQ ID NO:1, or contain an insufficient portion of such a domain (e.g. 10 amino acids or fewer) to result in retention of the polypeptide in a membrane-bound form.

"An isolated polypeptide consisting essentially of an amino acid sequence" means that the polypeptide can optionally have, in addition to said amino acid sequence, additional material covalently linked to either or both ends of the polypeptide, said additional material between 1 and 10,000 additional amino acids covalently linked to either or both ends of the polypeptide; or between 1 and 1,000 additional amino acids covalently linked to either or both ends of the polypeptide; or between 1 and 100 additional amino acids covalently linked to either or both ends of the polypeptide. Covalent linkage of additional amino acids to either or both ends of the polypeptide according to the invention results in a combined amino acid sequence that is not naturally occurring.

TNFR2 Polypeptides for Crystallization

TNFR2 polypeptides are polypeptides that comprise at least a portion of a TNFR2 (tumor necrosis factor receptor 2) polypeptide, or at least a portion of a variant thereof. TNFR2 polypeptides include TNFR2 fusion polypeptides, such as the TNFR2-Ig fusion polypeptides described below, as well as TNFR2:Fc polypeptides, etanercept, and variants, monomeric or multimeric forms, modified versions, and conjugates thereof.

The TNFR2 polypeptide has also been called TNFRSF1B (tumor necrosis factor receptor superfamily member 1B), p75, and CD120b; the full-length amino acid sequence of TNFR2 polypeptide is shown in SEQ ID NO:1 (see also Swiss-Prot Database Accession Number P20333). Another related but distinct tumor necrosis factor receptor is TNFR1, also called TNFRSF1A and p55 (see also Swiss-Prot Database Accession Number P19438). TNFR2 and TNFR1 are known to bind the pleiotropic cytokine tumor necrosis factor alpha (TNF-alpha or simply "TNF"), which is associated with inflammation. In addition to binding TNF-alpha, the TNFR2 and TNFR1 polypeptides mediate the binding to cells of homotrimers of TNF-beta (more commonly called "lymphotoxin-alpha", or LT-alpha), which is another cytokine associated with inflammation and which shares structural similarities with TNF-alpha (e.g., see Cosman, *Blood Cell Biochem* 7:51-77, 1996). As used herein, "TNFR" or "TNFR polypeptide" refers to a polypeptide that is capable of binding TNF-alpha or LT-alpha; specific examples of TNFR polypeptides are TNFR2 and TNFR1. As used herein, "binding", or "ligand binding", or "having ligand-binding activity" means binding a ligand such as TNF-alpha or LT-alpha with an affinity (that is, with an inhibition constant or $K_i$) of at least $1\times10^7$ $M^{-1}$ when in a monomeric form, or in further embodiments, with an affinity of at least $1\times10^8$ $M^{-1}$ when in a monomeric form, or with an affinity of at least $1\times10^9$ $M^{-1}$ when in the form of a multimer such as a dimer or trimer, or with an affinity of at least $8\times10^9$ $M^{-1}$ when in the form of a multimer such as a dimer or trimer. The TNF-alpha-binding affinity (inhibition constant) of a TNFR2 polypeptide or a variant thereof can be determined using a binding assay such as that described in Example 6 below (see also Mohler et al., 1993, *J Immunol* 151: 1548-1561 and Peppel et al., 1991, *J Exp Med* 174: 1483-1489). Similarly, analogous assays can be used to determine the binding affinity of a TNFR2 polypeptide or a variant thereof for LT-alpha or any other potential ligand. "TNFR-related", as used herein, refers to polypeptides that are related by amino acid sequence similarity or three-dimensional structural similarity to TNFR polypeptides, but which do not necessarily bind TNF-alpha or LT-alpha. Examples of TNFR-related polypeptides are CD40 (Swiss-Prot Database Accession Number P25942) and OX40 (Swiss-Prot Database Accession Number P43489) polypeptides.

The three-dimensional structures for TNFR1 and for some TNFR-related polypeptides have been determined; for example, the extracellular domain of the p55 TNFR1 has been crystallized and submitted to the Protein Data Bank (PDB, www.rcsb.org/pdb/) under the accession number 1EXT, and the p55 TNFR1 polypeptide in association with its ligand LT-alpha has been submitted to PDB as 1TNR. Also, in the Structural Classification of Proteins resource (SCOP, scop.berkeley.edu) the TNFR and TNFR-related polypeptides defining the SCOP TNF Receptor-Like protein fold are related structurally in that they share an extracellular domain having at least three similar disulphide-rich domains. For example, TNFR2 as shown in SEQ ID NO:1, has four such domains, with the most N-terminal three domains sharing a characteristic pattern of conserved cysteine residues that are involved in disulphide bond formation. The four disulphide-rich domains are at amino acids 39 through 76, at amino acids 77 through 118, at amino acids 119 through 162, and at amino acids 163 through 201 of SEQ ID NO:1. The disulphide bonds are formed between the pairs of cysteine residues at the following amino acid positions: 40 and 53, 54 and 67, 57 and 75, 78 and 93, 96 and 110, 100 and 118, 120 and 126, 134 and 143, 137 and 161, and (in the fourth domain) 164 and 179; the fourth disulfide bond domain also contains another pair of cysteine residues at amino acids 184 and 200 of SEQ ID NO:1.

TNFR2 polypeptides and variants thereof can be analyzed for their three-dimensional similarity to structurally characterized TNFR polypeptides and TNFR-related polypeptides by using computer programs such as GeneFold (Tripos, Inc., St. Louis, Mo.; Jaroszewski et al., 1998, *Prot Sci* 7: 1431-1440), a protein threading program that overlays a query protein sequence onto structural representatives within the Protein Data Bank (PDB) (Berman et al., 2000, *Nucleic Acids Res* 28: 235-242). To use GeneFold to assess the structure of a TNFR2 polypeptide or a variant thereof, the polypeptide sequence is entered into the program, which assigns a probability score that reflects how well it folds onto known protein structures ("template" structures) that are present in the GeneFold database. For scoring, GeneFold relies on primary amino acid sequence similarity, burial patterns of residues, local interactions, and secondary structure comparisons. The GeneFold program folds (or threads) the amino acid sequence onto all of the template structures in a database of protein folds, which includes the solved structures for several human TNFR polypeptides such as p55 TNFR1 (the template "1tnrR") and also the TNFR-related polypeptide CD40 (the template "1cdf_"). For each comparison, three different scores are calculated, based on (i) sequence only; (ii) sequence plus local conformation preferences plus burial terms; and (iii) sequence plus local conformation preferences plus burial terms plus secondary structure. In each instance, the program determines the optimal alignment, calculates the probability (P-value) that this degree of alignment occurred by chance, and reports the inverse of the P-value as the score. These scores therefore reflect the degree to which the query polypeptide sequence matches the various reference structures such as TNFR polypeptide structures. When using GeneFold to compare a TNFR2 polypeptide or variant thereof (the query polypeptide) to other TNFR or TNFR-related polypeptides, the query polypeptide will be matched to the 1cdf_, the 1tnrR, or another TNFR or TNFR-related template as the highest hit in one of the three scoring categories, and/or will be matched to a TNFR template with any score of at least 500, or at least 700, or at least 900, or at least 990, or 999.9 (the maximum score). Another method for analysis of a TNFR2 polypeptide or a variant thereof is alignment of the structure of that query polypeptide with those of TNFR or TNFR-related proteins through the well known process of homology modeling. One useful software program that can be used for homology modeling is the 'Modeler' program available from Accelrys, a subsidiary of Pharmacopeia Inc. (Princeton, N.J.).

The TNFR2 polypeptide for crystallization comprises at least a portion of the extracellular region of the TNFR2 polypeptide of SEQ ID NO:1, or a variant thereof. In certain embodiments, the entire extracellular region of the TNFR2 polypeptide is included in the TNFR2 polypeptide. As certain examples, the TNRF2 polypeptide can comprise amino acids 28 through 257, or amino acids 27 through 257, or amino acids 23 through 257 of SEQ ID NO:1. In further embodiments, the extracellular region of the TNFR2 polypeptide is truncated to delete at least one potential N-linked glycosylation site (e.g. amino acids 171 and 193 of SEQ ID NO:1) and/or a proline-rich region (e.g. amino acids 24 through 36 of SEQ ID NO:1 or amino acids 217 through 261 of SEQ ID NO:1) while leaving intact the three most N-terminal domains having intramolecular disulfide bridges. For example, in one embodiment, the TNFR2 polypeptide comprises amino acids 39 through 162 of SEQ ID NO:1, or amino acids 39 through 179 of SEQ ID NO:1, or amino acids 39 through 200 of SEQ ID NO:1, or a variant of any of the foregoing.

TNFR2 polypeptides for crystallization according to the present invention include polypeptides with amino acid sequence lengths that are at least 20% (or at least 25%, or at least 30%, or at least 35%, or at least 40%, or at least 50%) of the length of the TNFR2 polypeptide of SEQ ID NO:1 and have at least 60% sequence identity (or at least 70%, at least 75%, at least 80%, at least 85%, at least 90%, at least 95%, at least 97.5%, at least 99%, or at least 99.5%) with that TNFR2 polypeptide. Also included in the present invention are TNFR2 polypeptides and polypeptide fragments that contain a segment comprising at least 80, or at least 90, or at least 100, or at least 110, or at least 120, or at least 130 contiguous amino acids of SEQ ID NO:1, or a variant thereof. Such polypeptides and polypeptide fragments may also contain a segment that shares at least 70% sequence identity (or at least 70%, at least 75%, at least 80%, at least 85%, at least 90%, at least 95%, at least 97.5%, at least 99%, or at least 99.5%) with the TNFR2 polypeptide of SEQ ID NO:1.

When making such variants of the TNFR2 polypeptides to be crystallized, several considerations can be used to guide those of skill in the art in making variants that retain biological activity such as TNF-alpha-binding activity. In certain embodiments, it will be desirable to retain at least the three N-terminal disulfide bond regions, or at least all four of the disulfide bond regions described above for the TNFR2 polypeptide of SEQ ID NO:1. Further, portions of the TNFR2 extracellular domain that encompass the N-terminal three disulfide bond regions can be extended to include all or a portion of the fourth disulfide bond region, and in particular embodiments none of the cysteines of the fourth disulfide bond region are included, or a region of the fourth disulfide bond region including the first pair of cysteines (at amino acids 164 and 179 of SEQ ID NO:1) is included, and/or a region of the fourth disulfide bond region including the second pair of cysteines (at amino acids 185 and 200 of SEQ ID NO:1) is included. Therefore, variants encompassed within the scope of the invention retain the cysteine residues involved in forming the disulfide bonds of these domains, and also retain the approximate spacing (i.e. number of residues of the primary amino acid sequence) between those cysteines. For example, variants that do not insert or delete more than five amino acids between cysteine pairs that form disulfide bonds are within the scope of the invention, as are variants that do not insert or delete more than four amino acids between such cysteines, and variants that do not insert or delete more than three amino acids between such cysteines, and variants that do not insert or delete more than two amino acids between such cysteines, and variants that do not insert or delete more than one amino acid between such cysteines.

Another consideration that will guide those of skill in the art in making variants of TNFR2 polypeptides is the nature of the amino acid substitutions that are made; such substitutions can be conservative, which means that the amino acid present in the variant at a certain position has the same chemical and/or size properties as the amino acid at the corresponding position in the unaltered TNFR2 polypeptide. Table 2 summarizes groups of amino acids that are considered to have similar properties, so that the substitution of any amino acid with another from the same row of Table 2 would be a conservative substitution. In certain embodiments, TNFR2 polypeptide variants have 20% or fewer amino acid substitutions (or 15% or fewer, or 10% or fewer, or 7.5% or fewer, or 5% or fewer, or 2.5% or fewer, or 1% or fewer) across the length of amino acids 39 through 162 of SEQ ID NO:1, or of amino acids 39 through 179 of SEQ ID NO:1, or of amino acids 39 through 200 of SEQ ID NO:1. In certain embodiments, TNFR2 polypeptide variants have 20% or fewer conservative amino acid substitutions (or 15% or fewer, or 10% or fewer, or 7.5% or fewer, or 5% or fewer, or 2.5% or fewer, or 1% or fewer) across the length of amino acids 39 through 162 of SEQ ID NO:1, or of amino acids 39 through 179 of SEQ ID NO:1, or of amino acids 39 through 200 of SEQ ID NO:1.

In certain embodiments, the TNFR2 polypeptides or variants thereof to be crystallized have TNF-alpha-binding activity, and/or LT-alpha-binding activity.

TABLE 2

Conservative Amino Acid Substitutions

| | |
|---|---|
| Basic: | arginine; lysine; histidine |
| Acidic: | glutamic acid; aspartic acid |
| Polar: | glutamine; asparagine |
| Hydrophobic: | leucine; isoleucine; valine |
| Aromatic: | phenylalanine; tryptophan; tyrosine |
| Small: | glycine; alanine; serine; threonine; methionine |

TNFR2 Fusion Proteins

In certain embodiments, the TNFR2 polypeptides to be used in the crystallization methods of the invention include TNFR2 polypeptides fused to a portion of an Ig (immunoglobulin) polypeptide, or to a variant thereof, optionally with a polypeptide linker between the TNFR2 portion and the Ig portion of the TNFR2-Ig fusion polypeptide. (The optional polypeptide linker can be as short as one amino acid in length, when it is present in a TNFR2 fusion polypeptide.) Immunoglobulin (Ig) polypeptides are related by amino acid sequence and also by three-dimensional structure. The Ig superfamily of polypeptides, as defined in SCOP, is one subset of proteins having the protein fold "immunoglobulin-like beta-sandwich", which is described as generally having seven strands arranged in two sheets, although some members of the fold have additional strands. The Ig superfamily is subdivided into four families of protein domains: the V set domains (antibody variable domain-like); the C1 set domains (antibody constant domain-like); the C2 set domains; and the I set domains A TNFR2-Ig fusion polypeptide comprises at least a portion of an Ig polypeptide, for example, at least 10 contiguous amino acids of a constant region of an Ig polypeptide, or a polypeptide at least 14 amino acids in length that shares at least 70% amino acid identity with at least 20 contiguous amino acids of a constant region of an Ig polypeptide. A TNFR2-Ig fusion polypeptide of the present invention can preferably comprise at least one heavy chain constant region and, in certain embodiments, at least one light chain constant region.

In certain embodiments, the Ig polypeptide comprises the constant region of an IgG class heavy chain or a fragment and/or variant thereof, and in other embodiments the constant region of other immunoglobulin isotypes can be used to generate such TNFR2-Ig fusions. For example, a TNFR2-Ig fusion polypeptide comprising the constant region of an IgM class heavy chain or a fragment and/or variant thereof could be used to generate a decavalent form of the TNFR2-

Ig fusion polypeptide. The constant region of immunoglobulin heavy chains, with a specific example of a human IgG1 class heavy chain constant domain provided by SEQ ID NO:2, comprises a CH1 domain (amino acids 1 through 98 of SEQ ID NO:2), a hinge region (amino acids 99 through 110 of SEQ ID NO:2), a CH2 domain (amino acids 111 through 223 of SEQ ID NO:2), and a CH3 domain (amino acids 224 through 330 of SEQ ID NO:2). SEQ ID NO:3 provides a specific example of a variant of an IgG1 class heavy chain constant domain, in which two amino acid substitutions have been made (Glu has been substituted for Asp at position 239, and Met has been substituted for Leu at position 241). Certain embodiments of the invention include TNFR2-Ig fusion polypeptides comprising all or a portion of the extracellular domain of TNFR2 polypeptide (SEQ ID NO:1) fused to all or a portion of SEQ ID NO:2 or SEQ ID NO:3, optionally with a linker polypeptide between the TNFR2 portion and the Ig portion of the TNFR2-Ig fusion polypeptide. In further embodiments of the invention, a heavy chain constant region comprising at least a portion of $CH_1$ is the Ig portion of a TNFR2-Ig fusion polypeptide. Certain embodiments can also include, for example, the C-terminal half of the hinge region to provide a disulfide bridge between heavy chains. In certain embodiments of this invention, the TNFR2 polypeptide is covalently linked, optionally through a polypeptide linker, to the N-terminus of at least one portion of a $CH_1$ region of a heavy chain constant domain to form a TNFR2-Ig fusion polypeptide.

In certain additional embodiments, at least a portion of the hinge region is attached to the $CH_1$ region. As one example, $CH_1$ and $CH_2$ are present in the molecule, and the entire hinge region is also present. As another example $CH_1$ is present along with the first seven amino acids of the hinge (amino acids 99 through 105 of SEQ ID NO:2 or 3). It will be understood by one skilled in the art that the TNFR2-Ig fusion polypeptides of the invention can be, for example, monomeric or dimeric, and that if a dimeric TNFR2-Ig fusion polypeptide is desired, it is important to include the portion of the hinge region implicated in disulfide bond formation between the heavy chains (for example, a portion of amino acids 99 through 110 of SEQ ID NO:2 or 3 that includes amino acid 109 of SEQ ID NO:2 or 3). In further embodiments of the invention, the TNFR2-Ig fusion polypeptide can comprise portions of the CH3 domain that do not include the C-terminal lysine residue (amino acid 330 of SEQ ID NO:2 or 3), as this residue has been observed to be removed in post-translational processing of Ig heavy chain polypeptides.

Fc Domains

As used herein, an Fc domain can contain one or all of the heavy chain CH1, hinge, CH2, and CH3 domains described above, or fragments or variants thereof, and can be monomeric, dimeric, or multimeric as determined by the constituents of the TNFR2-Ig fusion polypeptide comprising the Fc domain.

Certain polypeptides specifically contemplated for crystallization according to the invention include TNFR2-Ig fusion polypeptides comprising at least a portion of an Fc domain. A preferred TNFR2 polypeptide suitable for treating diseases in humans and other mammals is TNFR2:Fc, which is used herein to refer to all or a portion of the extracellular domain of a TNFR2 polypeptide or a variant thereof, fused to the Fc portion of an immunoglobulin polypeptide, optionally with a polypeptide linker between the TNFR2 portion and the Fc portion of the TNFR2:Fc polypeptide.

Other Multimerizing Domains

Multimers of the invention include TNFR2 polypeptides for crystallization, wherein the TNFR2 polypeptides are in dimeric, trimeric, decameric, or other multimeric form. Another method for preparing the multimers of the invention involves use of a leucine zipper. Leucine zipper domains are peptides that promote oligomerization of the polypeptides in which they are found. Leucine zippers were originally identified in several DNA-binding polypeptides (Landschulz et al., *Science* 240:1759, 1988), and have since been found in a variety of different polypeptides. Among the known leucine zippers are naturally occurring peptides and derivatives thereof that dimerize or trimerize. The zipper domain (also referred to herein as a multimerizing, or multimer-forming, domain) comprises a repetitive heptad repeat, often with four or five leucine residues interspersed with other amino acids. Use of leucine zippers and preparation of multimers using leucine zippers are well known in the art. Other multimerization domains include the trimerization domain found in lung surfactant D protein (Kovacs et al., 2002, *J Biomol NMR* 24: 89-102) and other such domains known in the art.

Etanercept

In one embodiment, the TNFR2 polypeptide that is crystallized is "etanercept," which is a dimer of two polypeptides each consisting of 235 amino acids derived from the extracellular portion of the TNFR2 polypeptide, fused to a 232 amino acid portion of human IgG1. The amino acid sequence of the monomeric component of etanercept is shown as SEQ ID NO:4. In the dimeric form of this molecule, two of these fusion polypeptides (or "monomers") are held together by three disulfide bonds that form between the immunoglobulin portions of the two monomers. The etanercept dimer therefore consists of 934 amino acids, and has an apparent molecular weight of approximately 150 kilodaltons (Physicians Desk Reference, 2002, Medical Economics Company Inc., pp. 1752-1755). Etanercept is currently sold under the trade name ENBREL® (Amgen Inc., Thousand Oaks, Calif.).

Glycosylation and Conjugates

The invention includes TNFR2 polypeptides of the invention with or without associated native-pattern glycosylation. Polypeptides expressed in yeast or mammalian expression systems (e.g., COS-1 or CHO cells) can be similar to or significantly different from a native human polypeptide in molecular weight and glycosylation pattern, depending upon the choice of expression system. Expression of polypeptides of the invention in bacterial expression systems, such as *E. coli*, provides non-glycosylated molecules. Further, a given preparation can include multiple differentially glycosylated species of the polypeptide. Glycosyl groups can be removed through conventional methods, in particular those utilizing glycopeptidase. In general, glycosylated polypeptides of the invention can be incubated with a molar excess of glycopeptidase (Boehringer Mannheim).

A TNFR2 polypeptide for crystallization and use in the therapies described herein may be conjugated with polyethylene glycol (pegylated) to prolong its serum half-life or to enhance protein delivery. An example of a pegylated TNFR polypeptide derived from TNFR p55 is recombinant polyethylene glycol conjugated soluble TNFR p55 (PEG-sTNFR type I), which contains the extracellular domain of TNFR p55; TNFR2 polypeptides and fragments thereof can be conjugated with polyethylene glycol in a similar fashion. Reagents and methods for pegylation of polypeptides are described, for example, in WO 92/16221; WO 99/102330;

and U.S. Pat. Nos. 6,420,339; 6,433,158; 6,441,136; 6,451,986; 6,548,644; and 6,552,170; all of which are incorporated by reference herein.

The invention also encompasses crystalline forms of TNFR2 polypeptides conjugated to a cytotoxic or luminescent substance. Such substances include: maytansine derivatives (such as DM1); enterotoxins (such as a Staphylococcal enterotoxins); other toxic proteins and compounds (such as Ricin-A, *Pseudomonas* toxin, Diphtheria toxin, daunorubicin, doxorubicin, methotrexate, and Mitomycin C); iodine isotopes (such as iodine-125); technetium isotopes (such as Tc-99m); other isotopes ($^{212}$Bi, $^{131}$I, $^{186}$Re, and $^{90}$Y); cyanine fluorochromes (such as Cy5.5.18); and ribosome-inactivating polypeptides (such as bouganin, gelonin, or saporin-S6).

Producing and Purifying Polypeptides for Crystallization

The TNFR2 polypeptide can be produced by living host cells that express the polypeptide, such as host cells that have been genetically engineered to produce the polypeptide. Methods of genetically engineering cells to produce polypeptides are well known in the art. See, e.g., Ausubel et al., eds. (1990), Current Protocols in Molecular Biology (Wiley, New York). Such methods include introducing nucleic acids that encode and allow expression of the polypeptide into living host cells. These host cells can be bacterial cells, fungal cells, insect cells, or animal cells grown in culture. Bacterial host cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae*, *Pichia pastoris*, and *Aspergillus* cells. A few examples of animal cell lines that can be used are CHO, VERO, BHK, HeLa, Cos, MDCK, 293, 3T3, and W138. New animal cell lines can be established using methods well known by those skilled in the art (e.g., by transformation, viral infection, and/or selection). Optionally, the polypeptide can be secreted by the host cells into the medium.

Purification of the expressed TNFR2 polypeptide can be performed by any standard method. When the TNFR2 polypeptide is produced intracellularly, the particulate debris is removed, for example, by centrifugation or ultrafiltration. When the polypeptide is secreted into the medium, supernatants from such expression systems can be first concentrated using standard polypeptide concentration filters. Protease inhibitors can also be added to inhibit proteolysis and antibiotics can be included to prevent the growth of microorganisms. TNFR2 polypeptides can be produced in the presence of chaperone or accessory proteins in order to obtain a desired polypeptide conformation, or can be subjected to conditions such as oxidizing and/or reducing conditions after production in order to induce refolding or changes in polypeptide conformation (see, for example, WO 02/068455).

The TNFR2 polypeptide can be purified using, for example, hydroxyapatite chromatography, gel electrophoresis, dialysis, and affinity chromatography, and any combination of purification techniques known or yet to discovered. For example, protein A can be used to purify TNFR2-Ig polypeptides that are based on human gamma 1, gamma 2, or gamma 4 heavy chains (Lindmark et al., 1983, J. Immunol. Meth. 62:1-13), where the Ig portion of the TNFR2-Ig fusion polypeptide contains the portion of the constant domain involved in binding to protein A. Protein G is recommended for all mouse isotypes and for human gamma 3 (Guss et al., 1986, EMBO J. 5:1567-1575). Other techniques for TNFR2 polypeptide purification can be utilized, depending on need, including but not limited to fractionation on an ion-exchange column, precipitation with ethanol or other alcohols, reverse phase HPLC, FPLC, chromatography on silica, chromatography on heparin SEPHAROSET™, chromatography on an anion or cation exchange resin (such as a polyaspartic acid column), hydrophobic interaction chromatography, chromatofocusing, SDS-PAGE, and ammonium sulfate precipitation can also be utilized depending on need.

Production of Crystals, Crystal Formulations, and Compositions:

Polypeptide crystals are grown by controlled crystallization of polypeptides from aqueous solutions or from aqueous solutions containing organic solvents or additives. Solution conditions that may be controlled include, for example, the rate of evaporation of solvent, organic solvents or additives, the presence of appropriate co-solutes and buffers, pH, and temperature. A comprehensive review of the various factors affecting the crystallization of proteins has been published by McPherson, 1985, *Methods Enzymol* 114: 112-120. In addition, McPherson and Gilliland, 1988, *J Crystal Growth*, 90: 51-59 have compiled comprehensive lists of polypeptides that have been crystallized, as well as the conditions under which they were crystallized. A compendium of crystals and crystallization recipes, as well as a repository of coordinates of solved protein structures, is maintained by the Protein Data Bank at the Brookhaven National Laboratory (www.rcsb.org/pdb/; Bernstein et al., 1977, *J Mol Biol* 112: 535-542). These references can be used to determine the conditions necessary for crystallization of a polypeptide, as a prelude to the formation of appropriate polypeptide crystals and can guide the crystallization strategy for other polypeptide. It should be noted, however, that the conditions reported in most of the above-cited references have been optimized to yield, in most instances, a few large, diffraction quality crystals. Accordingly, it will be appreciated by those of skill in the art that some degree of adjustment of these conditions to provide a high yielding process for the large scale production of polypeptide crystals may be necessary.

In general, crystals are produced by combining the polypeptide to be crystallized with an appropriate aqueous solvent or aqueous solvent containing appropriate crystallization agents, such as salts or organic solvents or additives. The solvent is combined with the polypeptide and may be subjected to agitation at a temperature determined experimentally to be appropriate for the induction of crystallization and acceptable for the maintenance of polypeptide activity and stability. The solvent can optionally include co-solutes, such as divalent cations, co-factors, or chaotropes, as well as buffer species to control pH. "Co-solute means" for crystallization include compounds that can supply a co-solute to facilitate crystallization of a polypeptide. Examples of co-solute means include ammonium acetate, ammonium chloride, ammonium fluoride, ammonium formate, ammonium nitrate, ammonium phosphate, ammonium sulfate, cadmium chloride, cadmium sulfate, calcium acetate, calcium chloride, cesium chloride, cobaltous chloride, $CH_3(CH_2)_{15}N(CH_3)_3^+ Br^-$ (CTAB), di-ammonium citrate, di-ammonium hydrogen phosphate, di-ammonium phosphate, di-ammonium tartrate, di-potassium phosphate, di-sodium phosphate, di-sodium tartrate, DL-malic acid, ferric chloride, L-proline, lithium acetate, lithium chloride, lithium nitrate, lithium sulfate, magnesium acetate, magnesium chloride, magnesium formate, magnesium nitrate, magnesium sulfate, nickel chloride, potassium acetate, potassium bromide, potassium chloride, potassium citrate, potassium fluoride, potassium formate, potassium nitrate, potassium phosphate, potassium sodium tartrate, potassium sulfate, potassium thiocyanate, sodium acetate, sodium bromide, sodium chloride, sodium citrate, sodium fluoride, sodium formate, sodium malonate, sodium nitrate, sodium phosphate, sodium sulfate, sodium thiocyanate, succinic acid, tacsimate, tri-ammonium citrate, tri-lithium citrate, trimethylamine N-oxide, tri-potassium citrate, tri-sodium citrate, zinc acetate, zinc sulfate, and other compounds that function to supply co-solutes. "Crystallization buffering means" include compounds that maintain the pH of a solution in a desired range to facilitate crystallization of a polypeptide. Examples of crystallization buffering means include ACES (N-(2-acetamido)-2-aminoethanesulfonic acid), BES (N,N-bis(2-hydroxyethyl)-2-aminoethanesulfonic acid), Bicine (N,N-Bis(2-hydroxyethyl)glycine), BIS-TRIS (2,2-bis-(hydroxymethyl)-2,2',2"-nitrilotriethanol), boric acid, CAPS (3-[cyclohexylamino]-1-propanesulfonic acid), EPPS (HEPPS, 4-(2-Hydroxyethyl)piperazine-1-propanesulfonic acid), Gly-Gly ($NH_2CH_2CONHCH_2COOH$, glycyl-glycine), HEPES (4-(2-hydroxyethyl)piperazine-1-ethanesulfonic acid), imidazole, MES (2-morpholinoethanesulfonic acid), MOPS (3-(N-morpholino)-propanesulfonic acid), PIPES (piperazine-1,4-bis(2-ethanesulfonic acid)), sodium acetate, sodium bicarbonate, sodium phosphate monobasic (sodium dihydrogen phosphate), TAPS(N-[tris-(hydroxymethyl)methyl]-3-aminopropanesulfonic acid), TAPSO(N-[tris(hydroxymethyl) methyl]-3-amino-2-hydroxypropanesulfonic acid), TES (N-[tris(hydroxymethyl)methyl]-2-aminoethanesulfonic acid), Tricine (N-[tris(hydroxymethyl)methyl]glycine), Tris-HCl, TRIZMA (2-amino-2-(hydroxymethyl)-1,3-propanediol), and other compounds that function to maintain a solution at or near a specified pH.

The need for co-solutes, buffers, etc. and their concentrations are determined experimentally to facilitate crystallization. Some examples of suitable crystallization conditions for a polypeptide are described in Examples 1, 2, and 3 below.

In an industrial-scale process, the controlled precipitation leading to crystallization can best be carried out by the simple combination of polypeptide, precipitant, co-solutes and, optionally, buffers in a batch process. As another option, polypeptides may be crystallized by using polypeptide precipitates as the starting material ("seeding"). In this case, polypeptide precipitates are added to a crystallization solution and incubated until crystals form. Alternative laboratory crystallization methods, such as dialysis or vapor diffusion, can also be adopted. McPherson, supra and Gilliland, supra, include a comprehensive list of suitable conditions in their reviews of the crystallization literature. Occasionally, in cases in which the crystallized polypeptide is to be crosslinked, incompatibility between an intended crosslinking agent and the crystallization medium might require exchanging the crystals into a more suitable solvent system.

According to one embodiment of this invention, polypeptide crystals, crystal formulations and compositions are prepared by the following process: first, the polypeptide is crystallized. Next, excipients or ingredients as described herein are added directly to the mother liquor. Alternatively, the crystals are suspended in a solution of excipient or other formulary ingredients, after the mother liquor is removed, for a minimum of 1 hour to a maximum of 24 hours. The excipient concentration is typically between about 0.01 to 30% W/W, which corresponds to a polypeptide crystal concentration of 99.99 to 70% W/W, respectively. In one embodiment, the excipient concentration is between about 0.1 to 10%, which corresponds to a crystal concentration of 99.9 to 90% W/W, respectively. The mother liquor can be removed from the crystal slurry either by filtration or by centrifugation. Subsequently, the crystals are washed optionally with solutions of 50 to 100% one or more organic solvents or additives such as, for example, ethanol, methanol, isopropanol or ethyl acetate, either at room temperature or at temperatures between −20° C. to 25° C. The crystals are the dried either by passing a stream of nitrogen, air, or inert gas over the crystals. Alternatively, the crystals are dried by air drying or by lyophilization or by vacuum drying. The drying is carried out for a minimum 1 hour to a maximum of 72 hours after washing, until the moisture content of the final product is below 10% by weight, most preferably below 5%. Finally, micronizing of the crystals can be performed if necessary. The drying of polypeptide crystals is the removal of water, organic solvent or additive, or liquid polymer by means including drying with $N_2$, air, or inert gases; vacuum oven drying; lyophilization; washing with a volatile organic solvent or additive followed by evaporation of the solvent; or evaporation in a fume hood. Typically, drying is achieved when the crystals become a free-flowing powder. Drying may be carried out by passing a stream of gas over wet crystals. The gas may be selected from the group consisting of: nitrogen, argon, helium, carbon dioxide, air or combinations thereof. The polypeptide crystals of the invention can be further processed to achieve a desired particle size distribution by micronizing in a suitable mill, such as a jet mill, and the components of the particle or powder formulation may be mixed before or after micronizing. The diameter of the particles achieved can be in the range of 0.1 to 100 micrometers, or in the range of 0.2 to 10 micrometers, or in the range of 10 to 50 micrometers, or in the range of 0.5 to 2 micrometers. For formulations to be administered by inhalation, in one embodiment the particles formed from the polypeptide crystals are in the range of 0.5 to 1 micrometers.

According to one embodiment of this invention, when preparing protein crystals, protein crystal formulations or compositions, enhancers, such as surfactants are not added during crystallization. Excipients or ingredients are added to the mother liquor after crystallization, at a concentration of between about 1-10% W/W, alternatively at a concentration of between about 0.1-25% W/W, alternatively at a concentration of between about 0.1-50% W/W. These concentrations correspond to crystal concentrations of 99-90% W/W, 99.9-75% W/W and 99.9-50% W/W, respectively. The excipient or ingredient is incubated with the crystals in the mother liquor for about 0.1-3 hrs, alternatively the incubation is carried out for 0.1-12 hrs, alternatively the incubation is carried out for 0.1-24 hrs.

In another embodiment of this invention, the ingredient or excipient is dissolved in a solution other than the mother liquor, and the protein crystals are removed from the mother liquor and suspended in the excipient or ingredient solution. The ingredient or excipient concentrations and the incubation times are the same as those described above.

Polypeptide Crystals

As used herein, "crystal" or "crystalline" refers to one form of the solid state of matter, which is distinct from a second form—the amorphous solid state. Crystals display characteristic features including a lattice structure, characteristic shapes, and optical properties such as refractive index and birefringence. A crystal consists of atoms arranged in a pattern that repeats periodically in three dimensions (C. S. Barrett, Structure of Metals, 2nd ed., McGraw-Hill, New York, 1952, p.1). In contrast, amorphous material is a non-crystalline solid form of matter, sometimes referred to as an amorphous precipitate. Such precipitates have no molecular lattice structure characteristic of the crystalline solid state and do not display birefringence or other spectroscopic characteristics typical of the crystalline forms of matter.

Polypeptide crystals are polypeptide molecules arranged in a crystal lattice. Polypeptide crystals contain a pattern of specific polypeptide-polypeptide interactions that are repeated periodically in three dimensions. The polypeptide crystals of this invention are to be distinguished from amorphous solid forms or precipitates of polypeptides, such as those obtained by lyophilizing a polypeptide solution.

In polypeptide crystals, the polypeptide molecules form asymmetric units which are arranged together to form symmetric units. The geometric structure of the symmetric units of polypeptide crystals can be cubic, hexagonal, monoclinic, orthorhombic, tetragonal, triclinic, or trigonal. The overall structure of the crystals in their entirely can be in the form of bipyramids, cubes, needles, plates, prisms, rhomboids, rods, or spheres, or combinations thereof. Crystals that are of the "cubic" structural class can more specifically have octadecahedral or dodecahedral crystal forms. The diameter of the crystals is defined as the Martin's diameter. It is measured as the length of the line, parallel to the ocular scale, that divides the randomly oriented crystals into two equal projected areas. Crystals in forms such as needles or rods will also have a maximal dimension that is referred to herein as the length of the crystal.

Formulations for Therapeutic Administration

As used herein, a "composition" is understood to mean a mixture comprising at least two components. In particular, the invention provides compositions comprising a crystalline TNFR2 polypeptide, or prepared using a crystalline TNFR2 polypeptide. In one embodiment of the invention, the composition or formulation comprising or prepared using a crystalline TNFR2 polypeptide is prepared such that it is suitable for injection and/or administration to a patient in need thereof. Compositions to be administered for pharmaceutical purposes to patients are substantially sterile and do not contain any agents that are unduly toxic or infectious to the recipient.

In one embodiment of the invention, crystalline TNFR2 polypeptides such as crystalline etanercept are administered in the form of a physiologically acceptable composition (also referred to herein as a pharmaceutical composition or as a pharmaceutical formulation) comprising a crystalline TNFR2 polypeptide that is formulated with one or more of the following: physiologically acceptable carriers, excipients, or diluents. Such carriers, excipients, or diluents are nontoxic to recipients at the dosages and concentrations employed. Ordinarily, the preparation of such compositions entails combining the crystalline TNFR2 polypeptide with one or more of the following: buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and other stabilizers and excipients. In liquid formulations, neutral buffered saline or saline mixed with conspecific serum albumin are exemplary appropriate diluents. In accordance with appropriate industry standards, preservatives may also be added, such as benzyl alcohol. Further examples of components that may be employed in pharmaceutical formulations are presented in *Remington's Pharmaceutical Sciences*, 16th Ed., Mack Publishing Company, Easton, Pa., 1980, and in the *Handbook of Pharmaceutical Excipients*, published jointly by the American Pharmaceutical Association and the Pharmaceutical Society of Great Britain.

In one embodiment, it is contemplated that the formulation of the invention is prepared in a bulk formulation and as such, the components of the pharmaceutical composition are adjusted so that they are higher than would be required for administration, and are diluted appropriately prior to administration.

The polypeptide crystals of the present invention can be formulated as a solid crystalline or powder formulation in forms suitable for storage and handling, and in forms suitable for inhalation or pulmonary administration, for example in the form of powders for the preparation of aerosol formulations. In an further embodiment, the polypeptide crystals can be formulated in a liquid solution of such crystals, or in a slurry of such crystals. In another embodiment, the polypeptide crystals are used to prepare a liquid formulation, such as an aqueous formulation, for therapeutic administration.

Solid Crystalline Formulations

Solid formulations of crystals are ideally suited for pulmonary administration, which is particularly useful for biological macromolecules which are difficult to deliver by other routes of administration. (See, for example, PCT patent applications WO 96/32152, WO 95/24183 and WO 97/41833).

Solid formulations of polypeptide crystals include crystals that have been substantially isolated from liquid solution or dried, and are present as free crystals or as particles in for example powder form. In the present context the expression "powder" refers to a collection of essentially dry particles, i.e. the moisture content being below about 10% by weight, or below 6% by weight, or below 4% by weight. In one embodiment the invention provides a method for aerosolizing a dose of crystalline TNFR2 polypeptide comprising providing the crystalline TNFR2 polypeptide as a dry powder, dispersing an amount of the dry powder in a gas stream to form an aerosol, and capturing the aerosol in a chamber for subsequent inhalation.

Polypeptide crystals or powders can be optionally combined with carriers or surfactants. Suitable carrier agents include 1) carbohydrates, e.g. monosaccharides such as fructose, galactose, glucose, sorbose, and the like; 2) disaccharides, such as lactose, trehalose and the like; 3) polysaccharides, such as raffinose, maltodextrins, dextrans, and the like; 4) alditols, such as mannitol, xylitol, and the like; 5) inorganic salts, such as sodium chloride, and the like; and 6) organic salts, such as sodium citrate, sodium ascorbate, and the like. In certain embodiments, the carrier is selected from the group consisting of trehalose, raffinose, mannitol, sorbitol, xylitol, inositol, sucrose, sodium chloride, and sodium citrate. Surfactants can be selected from the group consisting of salts of fatty acids, bile salts or phospholipids. Fatty acids salts include salts of $C_{10-14}$ fatty acids, such as sodium caprate, sodium laurate, and sodium myristate. Bile salts include salts of ursodeoxycholate, taurocholate, glycocholate, and taurodihydrofusidate. In one embodiment, the surfactant is a salt of taurocholate such as sodium taurocholate. Phospholipids that can be used as surfactants include lysophosphatidylcholine. The molar ratio of crystalline polypeptide to surfactant in a powder formulation of the present invention is for example 9:1 to 1:9, or between 5:1 to 1:5, or between 3:1 to 1:3.

Crystals in Solution or Slurries

In one embodiment, this invention provides a method for rendering polypeptide crystals suitable for storage in suspensions comprising replacing the crystallization buffer (the mother liquor) with a non-aqueous solvent. In yet another embodiment, the crystalline slurry can be rendered solid by spinning out the first solvent and washing the remaining crystalline solid using a second organic solvent or additive to remove water, followed by evaporation of the non-aqueous solvent. Non-aqueous slurries of crystalline therapeutic proteins are especially useful for subcutaneous delivery.

In one such embodiment, the polypeptide crystals of the invention are combined with liquid organic additives with the object of stabilizing the polypeptide crystals. Such a mixture can be characterized as an aqueous-organic mixture that comprises n % organic additive, where n is between 1 and 99 and m % aqueous solution, where m is 100-n. Examples of organic additives include phenolic compounds, such as m-cresol or phenol or a mixture thereof, and acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alchohol, toluene, carbon tetrachloride, or combinations thereof.

Liquid Formulations

One embodiment of the present invention is directed to an aqueous formulation that allows for stable long-term storage of a pharmaceutical composition wherein a crystalline TNFR2 polypeptide is the active ingredient used in the preparation of the pharmaceutical composition. This formulation is useful, in part, because it is more convenient to use for the patient, as this formulation does not require any extra steps such as rehydrating. As used herein, a solution or liquid formulation is meant to mean a liquid preparation that contains one or more chemical substances dissolved in a suitable solvent or mixture of mutually miscible solvents.

Reconstitution is the dissolution of polypeptide crystals or crystal formulations or compositions in an appropriate buffer or pharmaceutical formulation.

Components of Pharmaceutical Formulations

The present pharmaceutical composition is prepared by combining, in addition to a crystalline TNFR2 polypeptide as described above, one or more of the following types of ingredients or excipients listed in the paragraphs below, many or all of which are available from commercial suppliers. It will be understood one of ordinary skill in the art that the combining of the various components to be included in the composition can be done in any appropriate order, namely, the buffer can be added first, middle or last and the tonicity modifier can also be added first, middle or last. It is also to be understood by one of ordinary skill in the art that some of these chemicals can be incompatible in certain combinations, and accordingly, are easily substituted with different chemicals that have similar properties but are compatible in the relevant mixture. There is knowledge in the art regarding the suitability of various combinations of excipients and other ingredients or materials present in, for example, the containers used for storage of the pharmaceutical composition and/or the devices used for therapeutic administration (see, for example, Akers, 2002, *J Pharm Sci* 91: 2283-2300).

Acidifying agents ("acidifying means"): acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid, and other suitable acids.

Active ingredients: additional active ingredients can also be included in the presently described composition, for example, to reduce injection site discomfort. Such active ingredients include, but are not limited to non-steroidal anti-inflammatory drugs such as, for example, tromethamine, in an appropriate dosage.

Aerosol propellants ("propellant means"): butane, dichlorodifluoromethane, dichlorotetrafluoroethane, isobutane, propane, trichloromonofluoromethane.

Aggregation inhibitors ("aggregation inhibiting means") reduce a polypeptide's tendency to associate in inappropriate or unwanted ternary or quaternary complexes. Suitable aggregation inhibitors include the amino acids L-arginine and/or, L-cysteine, which can act to reduce aggregation of polypeptides containing an Fc domain over long periods, e.g., two years or more. The concentration of the aggregation inhibitor in the formulation can be between about 1 MM to 1M, or about 10 mM to about 200 mM, or about 10 mM to about 100 mM, or about 15 MM to about 75 mM, or about 25 mM.

Alcohol denaturants ("denaturant means"!: denatonium benzoate, methyl isobutyl ketone, sucrose octacetate.

Alkalizing agents ("alkalizing means"): strong ammonia solution, ammonium carbonate, diethanolamine, diisopropanolamine, potassium hydroxide, sodium bicarbonate, sodium borate, sodium carbonate, sodium hydroxide, trolamine.

Anticaking agents ("anticaking means"): calcium silicate, magnesium silicate, colloidal silicon dioxide, talc.

Antifoaming agents ("antifoaming means"): dimethicone, simethicone.

Antioxidants ("antioxidant means") may be included in the formulations of the present invention. Anti-oxidants contemplated for use in the preparation of the formulations include amino acids such as glycine and lysine, chelating agents such as EDTA and DTPA, and free-radical scavengers such as sorbitol and mannitol. Additional antioxidants include ascorbic acid, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, sodium thiosulfate, sufur dioxide, tocopherol, and tocopherols excipient. Also contemplated for use in inhibiting oxidation is nitrogen or carbon dioxide overlay. Nitrogen or carbon dioxide overlay can be introduced to the headspace of a vial or prefilled syringe during the filling process.

Buffering agents ("formulation buffering means") maintain the pH of the pharmaceutical formulation in a desired range. When the pH of the pharmaceutical composition is set at or near physiological levels, comfort of the patient upon administration is maximized. In particular, in certain embodiments the pH of a pharmaceutical composition is within a pH range of about 4.0 to 8.4, or a pH range of about 5.0 to 8.0, or a pH range of about 5.8 to 7.4, or about 6.2 to 7.0. It is to be understood that the pH can be adjusted as necessary to maximize stability and solubility of the polypeptide in a particular formulation and as such, a pH outside of physiological ranges, yet tolerable to the patient, is within the scope of the invention. Various buffers suitable for use in the pharmaceutical composition of the invention include histidine, alkali salts (sodium or potassium phosphate or their hydrogen or dihydrogen salts), sodium citrate/citric acid, sodium acetate/acetic acid, potassium citrate, maleic acid, ammonium acetate, tris-(hydroxymethyl)-aminomethane (tris), various forms of acetate and diethanolamine, ammonium carbonate, ammonium phosphate, boric acid, lactic acid, phosphoric acid, potassium metaphosphate, potassium phosphate monobasic, sodium lactate solution, and any other pharmaceutically acceptable pH buffering agent known in the art. pH-adjusting agents such as hydrochloric acid, sodium hydroxide, or a salt thereof, may also be included in order to obtain the desired pH. One suitable buffer is sodium phosphate for maintaining pharmaceutical compositions at or near pH 6.2. In another example, acetate is a more efficient buffer at pH 5 than pH 6 so less acetate may be used in a solution at pH 5 than at pH 6. The concentration of the buffer in the formulation can be between about 1 mM to about 1M, or about 10 mM to about 200 mM.

Chelating agents ("chelating means", also called sequestering agents): edetate disodium, ethylenediaminetetraacetic acid and salts, edetic acid.

Coating agents ("coating means"): sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein.

Colors ("coloring means"): caramel; erythrosine (FD&C Red No. 3); FD&C Red No. 40; FD&C Yellow No. 5; FD&C Yellow No. 6; FD&C Blue No. 1; red, yellow, black, blue or blends; ferric oxide.

Complexing agents ("complex-forming means"): ethylenediaminetetraacetic acid and salts (EDTA), edetic acid, gentisic acid ethanolmaide, oxyquinoline sulfate.

Desiccants ("dessicating means"): calcium chloride, calcium sulfate, silicon dioxide.

Filtering aids ("filtering means"): powdered cellulose, purified siliceous earth.

Flavors and perfumes ("flavoring means"): anethole, anise oil, benzaldehyde, cinnamon oil, cocoa, ethyl vanillin, menthol, methyl salicylate, monosodium glutamate, orange flower oil, orange oil, peppermint, peppermint oil, peppermint spirit, rose oil, stronger rose water, thymol, tolu balsam tincture, vanilla, vanilla tincture, vanillin.

Humectants ("moisture-retaining means"): glycerin, hexylene glycol, propylene glycol, sorbitol.

Ointment bases ("ointment means"): lanolin, anhydrous lanolin, hydrophilic ointment, white ointment, yellow ointment, polyethylene glycol ointment, petrolatum, hydrophilic petrolatum, white petrolatum, rose water ointment, squalane.

Plasticizers ("plasticizing means"): castor oil, diacetylated monoglycerides, diethyl phthalate, glycerin, mono- and di-acetylated monoglycerides, polyethylene glycol, propylene glycol, triacetin, triethyl citrate.

Polymer membranes: cellulose acetate.

Polymeric carriers ("carrier means") are polymers used for encapsulation of polypeptide crystals for delivery of polypeptide, including biological delivery. Such polymers include biocompatible and biodegradable polymers. The polymeric carrier may be a single polymer type or it may be composed of a mixture of polymer types. Polymers useful as the polymeric carrier, include for example, poly(acrylic acid), poly(cyanoacrylates), poly(amino acids), poly(anhydrides), poly(depsipeptide), poly(esters) such as poly(lactic acid) or PLA, poly(lactic-co-glycolic acid) or PLGA, poly(B-hydroxybutryate), poly(caprolactone) and poly(dioxanone); poly(ethylene glycol), poly((hydroxypropyl)methacrylamide, poly [(organo)phosphazene], poly(ortho esters), poly(vinyl alcohol), poly(vinylpyrrolidone), maleic anhydride-alkyl vinyl ether copolymers, pluronic polyols, albumin, natural and synthetic polypeptides, alginate, cellulose and cellulose derivatives, collagen, fibrin, gelatin, hyaluronic acid, oligosaccharides, glycaminoglycans, sulfated polysaccharides, or any conventional material that will encapsulate polypeptide crystals.

Preservatives (or "preserving means"), such as antimicrobial preservatives, contemplated for use in the formulations of the present invention, such as multi-dose formulations, include benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol. The amount of preservative included will be in the range of 0% to 2% (w/v) or about 1% (w/v).

Solubilizing agents and stabilizers ("solubilizing means" or "stabilizing means", also refered to as emulsifying agents, co-solutes, or co-solvents) that increase the solubility of the polypeptide and/or stabilize the polypeptide while in solution (or in dried or frozen forms) can also be added to a pharmaceutical composition. Examples of solubilizing and stabilizing agents include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA (HSA), or recombinant HA), dextran, PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols (e.g., PEG, ethylene glycol and glycerol), dimethysulfoxide (DMSO), and dimethylformamide (DMF); amino acids such as: proline, L-methionine, L-serine, sodium glutamic acid, alanine, glycine, lysine hydrochloride, sarcosine, and gamma-aminobutyric acid; surfactants such as Tween-80, Tween-20, SDS, polysorbate, polyoxyethylene copolymer; and miscellaneous stabilizing excipients such as: potassium phosphate, sodium acetate, ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate; or any of the following: acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax; wetting and/or solubilizing agents such as benzalkonium chloride, benzethonium chloride, cetylpyridinium chloride, docusate sodium, nonoxynol 9, nonoxynol 10, octoxynol 9, polyoxyl 50 stearate, tyloxapol; or any combination of the above. The concentration of solubilizers/stabilizers in the formulation can be between about 0.001 to 5 weight percent, or about 0.1 to 2 weight percent. In one embodiment, the stabilizer is selected from sorbitan mono-9-octadecenoate poly(oxy-1,2-ethanediyl) derivatives, including but not limited to, polysorbate 80 or polysorbate 20. The amount of polysorbate 20 or 80 to be used in this embodiment is in the range of 0.001% to 0.1% (w/v), such as 0.005% (w/v), in single use or in multi-dose formulations. In another embodiment, free L-methionine in the range of 0.05 mM to 50 mM is included in the formulation: the amount of free L-methionine is 0.05 mM to 5 mM for single use formulations, and 1 mM to 10 mM for multi-dose formulations.

Solvents ("means for dissolving"): acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water.

Sorbents (also called adsorbents, "adsorbing means"): powdered cellulose, charcoal, purified siliceous earth; and carbon dioxide sorbents: barium hydroxide lime, soda lime.

Stiffening agents ("stiffening means"): hydrogenated castor oil, cetostearyl alcohol, cetyl alcohol, cetyl esters wax, hard fat, paraffin, polyethylene excipient, stearyl alcohol, emulsifying wax, white wax, yellow wax.

Suppository bases ("suppository means"): cocoa butter, hard fat, polyethylene glycol.

Suspending and/or viscosity-increasing agents ("viscosity-increasing means"): acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum.

Sweetening agents ("sweetening means"): aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup.

Tablet binders ("tablet binding means"): acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup.

Tablet and/or capsule diluents ("diluent means"): calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar.

Tablet disintegrants ("tablet disintegrant means"): alginic acid, microcrystalline cellulose, croscarmellose sodium, corspovidone, polacrilin potassium, sodium starch glycolate, starch, pregelatinized starch.

Tablet and/or capsule lubricants ("lubricating means"): calcium stearate, glyceryl behenate, magnesium stearate, light mineral oil, polyethylene glycol, sodium stearyl fumarate, stearic acid, purified stearic acid, talc, hydrogenated vegetable oil, zinc stearate.

Tonicity modifiers ("tonicity modifying means") are understood to be molecules that contribute to the osmolality of a solution. The osmolality of a pharmaceutical composition is preferably regulated in order to maximize the active ingredient's stability and also to minimize discomfort to the patient upon administration. Serum is approximately 300+/− 50 milliosmolals per kilogram. It is generally preferred that a pharmaceutical composition be isotonic with serum, i.e., having the same or similar osmolality, which is achieved by addition of a tonicity modifier, thus it is contemplated that the osmolality will be from about 180 to about 420 milliosmolals, however, it is to be understood that the osmolality can be either higher or lower as specific conditions require. Examples of tonicity modifiers suitable for modifying osmolality include, but are not limited to amino acids (e.g., arginine, cysteine, histidine and glycine), salts (e.g., sodium chloride, potassium chloride and sodium citrate) and/or saccharides (e.g., sucrose, glucose, dextrose, glycerin, and mannitol). The concentration of the tonicity modifier in the formulation can be between about 1 mM to 1M, or about 10 mM to about 200 mM. In one embodiment, the tonicity modifier is sodium chloride within a concentration range of 0 mM to 200 mM. In another embodiment, the tonicity modifier is sorbitol or trehalose and no sodium chloride is present.

Vehicles ("vehicle means"): flavored and/or sweetened (aromatic elixir, compound benzaldehyde elixir, iso-alcoholic elixir, peppermint water, sorbitol solution, syrup, tolu balsam syrup); oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); solid carriers such as sugar spheres; sterile (bacteriostatic water for injection, bacteriostatic sodium chloride injection).

Water-repelling agent ("water-repelling means"): cyclomethicone, dimethicone, simethicone.

In certain embodiments, the pharamceutical composition comprises a compound selected from the following, or any combination thereof: salts of 1) amino acids such as glycine, arginine, aspartic acid, glutamic acid, lysine, asparagine, glutamine, proline; 2) carbohydrates, e.g. monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-β-cyclodextrin and alike; 8) inorganic salts, such as sodium chloride, potassium chloride, magnesium chloride, phosphates of sodium and potassium, boric acid ammonium carbonate and ammonium phosphate; 9) organic salts, such as acetates, citrate, ascorbate, lactate; 10) emulsifying or solubilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol; and 12) particular ingredients such as sucrose, trehalose, lactose, sorbitol, lactitol, inositol, salts of sodium and potssium such as acetate, phosphates, citrates, borate, glycine, arginine, polyethylene oxide, polyvinyl alcohol, polyethylene glycol, hexylene glycol, methoxy polyethylene glycol, gelatin, hydroxypropyl-β-cyclodextrin.

Sustained-Release Forms

In one preferred embodiment of the invention, sustained-release forms (also called "controlled-release" forms) of crystalline TNFR2 polypeptides are used, including sustained-release forms of crystalline TNFR2:Fc; sustained- or controlled-release forms comprise crystalline polypeptide and a substance (the "sustained-release means") for extending the physical release or biological availability of the crystalline polypeptide over a desired period of time. Sustained-release forms suitable for use in the disclosed methods include, but are not limited to, crystalline TNFR2 polypeptides that are encapsulated in sustained-release means such as a slowly-dissolving biocompatible polymer (for example, the polymeric carriers described herein, the alginate microparticles described in U.S. Pat. No. 6,036,978, or the polyethylene-vinyl acetate and poly(lactic-glucolic acid) compositions described in U.S. Pat. No. 6,083,534), admixed with such a polymer (including topically applied hydrogels), and or encased in a biocompatible semi-permeable implant. Further embodiments of the invention include additional sustained-release forms such as polymeric microparticles, wherein a mixture of the active ingredient and sustained-release means such as polymers (for example, PLGA) are dispersed within a continuous phase, and the resulting dispersion is directly lyophilized to remove water and organic solvents or additives and form said microparticles (U.S. Pat. No. 6,020,004); injectable gel compositions comprising a biodegradable anionic polysaccharide such as an alginate ester, a polypeptide, and at least one bound polyvalent metal ion (U.S. Pat. No. 6,432,449); injectable biodegradable polymeric matrices having reverse thermal gelation properties and optionally pH-responsive gelation/de-gelation properties (U.S. Pat. Nos. 6,541,033 and 6,451,346); biocompatible polyol:oil suspensions, such as those wherein the suspension comprises polyol in the range of from about 15% to about 30% by weight (U.S. Pat. No. 6,245,740). Such sustained release forms are suitable for continuous delivery of polypeptides through administration in the form of a depot, wherein the depot can be an implant, or can be in the form of injectable microspheres, nanospheres, or gels. The above listed U.S. patents (U.S. Pat. Nos. 6,036,978; 6,083,534; 6,020,004; 6,432,449; 6,541,033; 6,451,346, and 6,245,740) are incorporated in their entirety by reference herein. In addition, sustained- or controlled-release forms of crystalline polypeptides of the invention comprise types of sustained release means such as those described in Kim, C., 2000, "Controlled Release Dosage Form Design", Techonomic Publishing Co., Lancaster Pa., which include the following: natural polymers (gelatin, sodium alginic acid, xanthan gum, arabic gum, or chitosan), semi-synthetic polymers or cellulose derivatives (methylcellulose, ethylcellulose, hydroxyethylcellulose, hydroxypropylcellulose, hydroxyethylmethylcellulose, hydroxypropylmethylcellulose, sodium carboxymethylcellulose, cellulose acetate, cellulose acetate butyrate, cellulose acetate proprionate, cellulose acetatephthalate, or hydroxypropylmethylcellulose phthalate), and synthetic polymers (ion exchange resins (methacrylic acid, sulfonated polystyrene/divinylbenzene), polyacrylic acid (Carbopol), poly (MMA/MAA), poly(MMA/DEAMA), poly(MMA/EA), poly(vinylacetate phthalate), poly(vinyl alcohol), poly(vinyl pyrrolidone), poly(lactic acid), poly(glycolic acid), poly (lactic/glycolic acid), polyethylene glycol, polyethylene oxide, poly(dimethyl silicone), poly(hydroxyethyl methacrylate), poly(ethylene/vinyl acetate), poly(ethylene/vinyl alcohol), polybutadiene, poly(anhydride), poly(orthoester), and poly(glutamic acid)).

Further embodiments of the invention include TNFR2 polypeptide crystals encapsulated in at least one polymeric carrier to form microspheres by virtue of encapsulation within the matrix of the polymeric carrier to preserve their native and biologically active tertiary structure, as described in U.S. Pat. No. 6,541,606, which is incorporated in its entirety by reference herein. TNFR2 polypeptide crystals or formulations thereof to be encapsulated are suspended in a polymeric carrier such as PLGA which is dissolved in an organic solvent or additive. Such encapsulated TNFR2 polypeptide crystals maintain the biological activity of the TNFR2 polypeptide for a longer period of time than TNFR2 polypeptides in solution when stored under comparable conditions.

Illustrative Embodiments

The formulation can comprise about 25 to about 50 mg TNFR2 polypeptide or etanercept, wherein the TNFR2 polypeptide or etanercept are reconstituted from crystalline forms, about 10 mM to about 100 mM L-arginine, about 10 mM to about 50 mM sodium phosphate, about 0.75% to about 1.25% sucrose, about 50 mM to about 150 mM NaCl, at about pH 6.0 to about pH 7.0. In another embodiment L-arginine can be replaced with L-cysteine (at about 1 to about 500 micromolar) in the formulation. In another embodiment, the pH can be about pH 7.0. In another embodiment, the pharmaceutical composition comprises 25 mg/mL crystalline TNFR2, about 25 mM L-arginine, about 25 mM sodium phosphate, about 98 mM sodium chloride, and about 1% sucrose at pH 6.2. In another embodiment, wherein the crystalline etanercept or the etanercept reconstituted from crystalline form has a higher level of biological activity per unit of etanercept than non-crystallized etanercept preparations, the formulation can comprise about 10 to about 50 mg crystalline etanercept or etanercept reconstituted from crystalline form, or about 15 to about 25 mg crystalline etanercept or etanercept reconstituted from crystalline form.

Testing Formulations for Polypeptide Stability and Biological Activity

In yet another embodiment, the invention provides a method for accelerated stability testing of the stability of a crystalline TNFR2 polypeptide in a pharmaceutical composition of the invention comprising the steps of testing the activity of the polypeptide formulated according to the invention prior to storage, i.e., time zero; storing the composition at 37° C. for one month and measuring the stability of the polypeptide; and comparing the stability form time zero to the one month time point. This information is helpful for early elimination of batches or lots that appear to have good stability initially, yet do not store well for longer periods.

Moreover, the present pharmaceutical composition provides improved long-term storage such that the active ingredient, e.g., a crystalline TNFR2 polypeptide, is stable over the course of storage either in liquid or frozen states. As used herein, the phrase "long-term" storage is understood to mean that the pharmaceutical composition can be stored for three months or more, for six months or more, and preferably for one year or more. Long term storage is also understood to mean that the pharmaceutical composition is stored either as a liquid at 2-8° C. or is frozen, e.g., at −20° C. or colder. It is also contemplated that the composition can be frozen and thawed more than once. The term "stable" with respect to long-term storage is understood to mean that the active polypeptide of the pharmaceutical composition does not lose more than 20%, or more preferably 15%, or even more preferably 10%, and most preferably 5% of its activity relative to activity of the composition at the beginning of storage. Activity of the TNFR2 polypeptide can be assayed by any one of a number of assays, including ligand-binding assays such as ELISA assays, where ligand is bound to a solid support, test and control preparations of TNFR2 polypeptides are added, and binding of the TNFR2 polypeptide to the ligand is detected using labeled anti-Ig antibodies directed to the Ig component of the TNFR2 polypeptide. In addition, assays such as those described in Example 6 can be used to detect biological activity of TNFR2 polypeptides that bind TNF, or can be modified to test activity of TNFR2 polypeptides that bind other ligands.

Administration and Dosing

As used herein, "administration of crystalline TNFR2" or "administration of crystalline TNFR2 polypeptides" means the administration of a pharmaceutical composition comprising crystalline TNFR2 polypeptides, or prepared using crystalline TNFR2 polypeptides.

Any efficacious route of administration may be used to therapeutically administer crystalline TNFR2. If injected, crystalline TNFR2 can be administered, for example, via intraarticular, intravenous, intramuscular, intralesional, intraperitoneal, or subcutaneous routes by bolus injection or by continuous infusion. Other suitable means of administration include sustained release from implants, depots (implanted or injected), suppositories, aerosol inhalation, eyedrops, oral preparations, including pills, syrups, lozenges, or chewing gum, and topical preparations such as lotions, gels, sprays, ointments, or other suitable techniques. When crystalline TNFR2 is administered in combination with one or more other biologically active compounds, these may be administered by the same or by different routes, and may be administered simultaneously, separately, or sequentially.

Appropriate dosages can be determined in standard dosing trials, and may vary according to the chosen route of administration. The amount and frequency of administration will depend on such factors as the nature and severity of the indication being treated, the desired response, the age and condition of the patient, and so forth. In the following dosing regimens, the amount of crystalline TNFR2 administered is understood to be the amount of crystalline TNFR2 for pharmaceutical compositions comprising crystalline TNFR2, or the amount of TNFR2 polypeptide for pharmaceutical compositions prepared using crystalline TNFR2.

In one embodiment of the invention, crystalline TNFR2 is administered one time per week to treat a medical disorder or condition disclosed herein, in another embodiment is administered at least two times per week, and in another embodiment is administered at least three times per week. An adult patient is a person who is 18 years of age or older. If injected, the effective amount of crystalline TNFR2 per adult dose ranges from 1-20 mg/m$^2$ of body surface area, and preferably is about 5-12 mg/m$^2$. Alternatively, a flat dose may be administered, whose amount may range from 5-100 mg/dose. Exemplary dose ranges for a flat dose to be administered by subcutaneous injection are 5-25 mg/dose, 25-50 mg/dose, and 50-100 mg/dose. In one embodiment of the invention, the various indications described below are treated by administering a preparation acceptable for injection containing or prepared from crystalline TNFR2 at 25 mg TNFR2 per dose, or alternatively, containing 50 mg per dose. The 25 mg or 50 mg dose may be administered repeatedly, particularly for chronic conditions. If a route of administration other than injection is used, the dose is appropriately adjusted in accord with standard medical practices. In many instances, an improvement in a patient's condition will be obtained by injecting a dose of about 25 mg of crystalline TNFR2 one to three times per week over a period of at least three weeks, or a dose of 50 mg of crystalline TNFR2 one or two times per week for at least three weeks, though treatment for longer periods may be necessary to induce the desired degree of improvement. For incurable chronic conditions, the regimen may be continued indefinitely, with adjustments being made to dose and frequency if such are deemed necessary by the patient's physician.

For pediatric patients (age 4-17), a suitable regimen involves the subcutaneous injection of 0.4 mg/kg of body weight, up to a maximum of 25 mg per dose of crystalline TNFR2, administered by subcutaneous injection one or more times per week.

In addition to human patients, crystalline TNFR2 polypeptides are useful in the treatment of medical conditions as described herein afflicting non-human animals, such as pets (dogs, cats, birds, primates, etc.), domestic farm animals (horses cattle, sheep, pigs, birds, etc.), or any animal that suffers from a condition comparable to one of the conditions described herein. In such instances, an appropriate dose may be determined according to the animal's body weight. For example, a dose of 0.2-1 mg/kg may be used. Alternatively, the dose is determined according to the animal's surface area, an exemplary dose ranging from 0.1-20 mg/m$^2$ of body surface area, or more preferably, from 5-12 mg/m$^2$ of body surface area. For small animals, such as dogs or cats, a suitable dose is 0.4 mg/kg of body weight. In another embodiment, crystalline TNFR2 (where the TNFR2 polypeptide is preferably expressed from genes derived from the same species as the patient) is administered by injection or other suitable route one or more times per week until the animal's condition is improved, or it may be administered indefinitely.

In another embodiment, wherein the crystalline TNFR2 polypeptide or the TNFR2 polypeptide reconstituted from crystalline form has a higher level of biological activity per unit of TNFR2 polypeptide than non-crystallized TNFR2 polypeptide preparations, the dosages given above can be reduced appropriately, based on the degree of increase in biological activity of the crystalline TNFR2 polypeptide. For example, the dosages above can be reduced to 50% of the above dosages and dosage ranges if crystallization increases biological activity two-fold per unit of TNFR2 polypeptide; in other embodiments, the dosages are reduced to 10 to 95% of the above dosages, or to 25 to 75% of the above dosages, or to 60% or 70% or 80% of the above dosages.

The invention further includes the administration of crystalline TNFR2 concurrently with one or more other drugs that are administered to the same patient in combination with the pharmaceutical composition comprising crystalline TNFR2 polypeptides, or prepared using crystalline TNFR2 polypeptides, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components may be administered in the same or in separate compositions, and by the same or different routes of administration.

Therapeutic Uses

The invention pertains to methods for treating various medical disorders by administering crystalline TNFR2 polypeptides. The crystalline TNFR2 polypeptides may be administered in combination with other biologically active molecules, in a manner exemplified by, but not limited to, the combination and/or concurrent therapies described herein. This invention provides compounds, compositions, and methods for treating a mammalian patient, including a human patient, who is suffering from a medical disorder. For purposes of this disclosure, the terms "illness," "disease," "medical condition," "abnormal condition" and the like are used interchangeably with the term "medical disorder."

In accordance with this invention, patients having medical disorders are administered a therapeutically effective amount of a crystalline TNFR2 polypeptide. The crystalline TNFR2 polypeptide can be the crystalline form of a TNF-alpha-binding soluble TNF-alpha receptor such as crystalline TNFR2:Fc. As used herein, the phrase "administering a therapeutically effective amount" of a therapeutic agent means that the patient is treated with the agent in an amount and for a time sufficient to induce a sustained improvement over baseline in at least one indicator that reflects the severity of the disorder. An improvement is considered "sustained" if the patient exhibits the improvement on at least two occasions separated by one or more weeks. The degree of improvement is determined based on signs or symptoms, and determinations may also employ questionnaires that are administered to the patient, such as quality-of-life questionnaires. Various indicators that reflect the extent of the patient's illness may be assessed for determining whether the amount and time of the treatment is sufficient. The baseline value for the chosen indicator or indicators is established by examination of the patient prior to administration of the first dose of the crystalline etanercept or other crystalline TNFR2 polypeptide. Preferably, the baseline examination is done within about 60 days of administering the first dose. If the crystalline TNFR2 polypeptide is being administered to treat acute symptoms, such as for example to treat a traumatic knee injury, the first dose is administered as soon as practically possible after the injury has occurred.

Improvement is induced by administering crystalline TNFR2 polypeptide until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions. For injuries or acute conditions, a single dose may be sufficient. Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

In one embodiment, the medical disorders to be treated with crystalline TNFR2 polypeptides are characterized by abnormal or excessive TNF-alpha levels. It has been proposed that a systemic or localized excess of TNF-alpha contributes to the progression of numerous medical disorders. For example, patients with chronic heart failure have elevated levels of serum TNF-alpha, which have been shown to increase with disease progression (see, for example, Levine et al., *N Eng J Med* 323:236-241, 1990). A variety of other diseases are associated with elevated levels of TNF-alpha (see, for example, Feldman et al., *Transplantation Proceedings* 30:4126-4127, 1998). It has been suggested that the suppression of TNF-alpha might be beneficial in patients suffering from disorders characterized by abnormal or excessive TNF-alpha expression. However, although progress has been made in devising effective treatment for such diseases, improved medicaments and methods of treatment are needed.

Provided herein are methods for treating a number of medical disorders characterized by abnormal TNF-alpha expression by administering crystalline TNFR2 polypeptides, such as the crystalline form of a soluble TNF-alpha receptor such as TNFR2:Fc, for a period of time sufficient to induce a sustained improvement in the patient's condition. The subject methods involve administering to the patient a formulation comprising, or prepared using, a crystalline TNFR2 polypeptide that is capable of reducing the effective amount of endogenous biologically active TNF-alpha, such as by preventing the binding of TNF-alpha to its cell surface receptor (TNFR).

Cardiovascular Disorders

Cardiovascular disorders are treatable with the disclosed crystalline TNFR2 polypeptides, pharmaceutical compositions thereof, and/or combination therapies. Examples of cardiovascular disorders treatable with a crystalline TNFR2 polypeptide, such as crystalline TNFR2:Fc, include: aortic aneurisms; arteritis; vascular occlusion, including cerebral artery occlusion; complications of coronary by-pass surgery; ischemia/reperfusion injury; heart disease, including atherosclerotic heart disease, myocarditis, including chronic autoimmune myocarditis and viral myocarditis; heart failure, including chronic heart failure (CHF), cachexia of heart failure; myocardial infarction; restenosis after heart surgery; silent myocardial ischemia; post-implantation complications of left ventricular assist devices; Raynaud's phenomena; thrombophlebitis; vasculitis, including Kawasaki's vasculitis; giant cell arteritis, Wegener's granulomatosis; and Schoenlein-Henoch purpura.

In addition, TNFR2:Fc or the other crystalline TNFR2 polypeptides disclosed herein may be used in combination with myeloid or angiogenic stem cell therapies for the treatment of cardiovascular disease, including cardiomyopathy of ischemic or non-ischemic origin, post-myocardial infarction angiogenic therapy or treatment for peripheral arterial disease. Stem cells useful for this purpose include mesenchymal stem cells and endothelial precursor cells, such as those found in spleen, fetal liver, bone marrow or circulating blood (U.S. Pat. No. 5,486,359; Deisher T, *Drugs* 3(6):649-53 (2000); Huss R, *Stem Cells* 18:1-9 (2000); Huss et al., *Stem Cells* 18:252-60 (2000)). The crystalline TNFR2 polypeptides may be given concurrently with stem cell transplants as well as treatments with proliferative or differentiative stem cell growth factors.

TNF-alpha and IL-8 have been implicated as chemotactic factors in atherslcerotic abdominal aortic aneurism (Szekanecz et al., *Pathobiol* 62:134-139 (1994)). Abdominal aortic aneurism may be treated in human patients by administering a crystalline TNFR2 polypeptide, such as crystalline TNFR2:Fc, which may be administered in combination with an inhibitor of IL-8, such treatment having the effect of reducing the pathological neovascularization associated with this condition.

Studies have shown that metalloproteinases (MMPs) are a key element in myocardial remodeling and fibrosis. Thus, administering crystalline TNFR2 polypeptides to inhibit TNF-alpha and the inflammatory response in conjunction with direct inhibition of MMPs will reduce, prevent, or reverse disorders such as left ventricular pump dysfunction. This is accomplished by co-administering a crystalline TNFR2 polypeptide, such as crystalline TNFR2:Fc, together with an MMP inhibitor. Alternatively, treatment of left ventricular pump dysfunction may involve administering a crystalline TNFR2 polypeptide without the concurrent use of an MMP inhibitor.

Any of the disclosed crystalline TNFR2 polypeptides or combination treatments disclosed herein also may be used to treat familial combined hyperlipidemia (FCH). FHC is a genetic dyslipidemia characterized by premature coronary heart disease. FCH patients are genetically defective in their TNFR II gene, have low levels of sTNFR II levels in their bodies and appear to be hyperresponsive to the deleterious effects of endogenous TNF-alpha (van Greevenbroek et al., 2000, *Atherosclerosis* 153: 1-8). Coronary heart disease, insulin resistance and obesity associated with FCH can be ameliorated or prevented by administering to FCH patients any one of the crystalline TNFR2 polypeptides disclosed herein, such as crystalline TNFR2:Fc or crystalline etanercept. In addition, crystalline TNFR2 polypeptide treatment for FCH may be administered concurrently with reduction of dietary fat and cholesterol and/or with one or more of the other drugs used to treat this condition, including bile acid-sequestering resins (cholestyramine and colestipol), nicotinic acid, niacin, a cholesterol-lowering drug, such as gemfibrozil or probucol, or one of the cholesterol-lowering "statin" or HMG-CoA reductase inhibitors, such as lovastatin or pravastatin. In another aspect of the invention, crystalline TNFR2 polypeptides are used to treat patients who have elevated serum levels of C-reactive protein (CRP) and who thus are at risk for heart attack even when their cholesterol may be low (Ridker et al., 2001, *New Eng J Med* 344: 1959-1965).

Infections and Injuries

The disclosed crystalline TNFR2 polypeptides, compositions, and/or combination therapies described herein are useful in medicines for treating bacterial, viral or protozoal infections, and complications resulting therefrom. One such disease is *Mycoplasma pneumonia*. In addition, provided herein is the use of crystalline TNFR2 polypeptides to treat AIDS and related conditions, such as AIDS dementia complex, AIDS associated wasting, lipidistrophy due to antiretroviral therapy; and Kaposi's sarcoma. Provided herein is the use of crystalline TNFR2 polypeptides for treating protozoal diseases, including malaria (including cerebral malaria) and schistosomiasis. Additionally provided is the use of crystalline TNFR2 polypeptides to treat erythema nodosum leprosum; bacterial or viral meningitis; tuberculosis, including pulmonary tuberculosis; and pneumonitis secondary to a bacterial or viral infection. Provided also herein is the use of crystalline TNFR2 polypeptides to prepare medicaments for treating louse-borne relapsing fevers, such as that caused by *Borrelia recurrentis*. Crystalline TNFR2 polypeptides can also be used to prepare a medicament for treating conditions caused by Herpes viruses, such as herpetic stromal keratitis, corneal lesions, and virus-induced corneal disorders. In addition, crystalline TNFR2 polypeptides can be used in treating human papillomavirus infections, as well as in treating infectious mononucleosis. Crystalline TNFR2 polypeptides are used also to prepare medicaments to treat influenza, as well as to treat critical illness polyneuropathy and myopathy (CIPNM), an inflammatory syndrome that occasionally occurs in conjunction with prolonged septic illnesses. The subject crystalline TNFR2 polypeptides are used also to treat transmissible spongiform encephalopathies, which is believed to be mediated by prions.

Another disorder that can be treated with any of the disclosed crystalline TNFR2 polypeptides, pharmaceutical compositions thereof, and/or combination therapies is tropical spastic paraparesis/HTLV-1 associated myelopathy (TSP/HAM). This disease is caused by infection with the human retrovirus HTLV-1. Recent studies have suggested that TNF-alpha may play a role in the decreased glutamate uptake exhibited by HTLV-infected cells (Szymocha et al., 2000, *J Virol* 74: 6433-6441). TSP/HAM is a slowly progressing condition of the spinal cord that causes weakness and muscle stiffness in the legs, often accompanied by a loss of sensation in the feet. Known treatments for this condition include corticosteroids and plasmapheresis. TSP/HAM may be treated with any of the crystalline TNFR2 polypeptides disclosed herein, any of which may be administered concurrently with a corticosteroid, plasmapheresis, or both. An exemplary crystalline TNFR2 polypeptide for treating TSP/HAM is crystalline TNFR2:Fc. Sufficiency of treatment is determined by monitoring the patient for improvement in leg strength, or an arrest of the patient's deterioration or by any other means deemed appropriate by the patient's physician.

Other conditions treatable by the disclosed crystalline TNFR2 polypeptides, compositions, and/or combination therapies include those resulting from injuries to the head or spinal cord, and including subdural hematoma due to trauma to the head.

Neurolozic Disorders, Pain, and Fever

Cervicogenic headache is a common form of headache arising from dysfunction in the neck area, and which is associated with elevated levels of TNF-alpha, which are believed to mediate an inflammatory condition that contributes to the patient's discomfort (Martelletti, *Clin Exp Rheumatol* 18(2 Suppl 19):S33-8 (March-April, 2000)). Cervicogenic headache may be treated by administering crystalline TNFR2 polypeptides as disclosed herein, thereby reducing the inflammatory response and associated headache pain.

In addition, the subject crystalline TNFR2 polypeptides, compositions, and/or combination therapies are used to treat chronic pain conditions, such as chronic pelvic pain, including chronic prostatitis/pelvic pain syndrome. As a further example, crystalline TNFR2 polypeptides, compositions, and/or combination therapies of the invention are used to treat post-herpetic pain.

The crystalline TNFR2 polypeptides, compositions, and/or combination therapies of the invention are useful for treating primary amyloidosis. In addition, the secondary amyloidosis that is characteristic of various conditions also are treatable with crystalline TNFR2 polypeptides such as crystalline TNFR2:Fc, and the compositions and/or combination therapies described herein. Such conditions include: Alzheimer's disease, secondary reactive amyloidosis; Down's syndrome; and dialysis-associated amyloidosis. Also treatable with the compounds, compositions, and/or combination therapies of the invention are inherited periodic fever syndromes, including familial Mediterranean fever, hyperimmunoglobulin D and periodic fever syndrome and TNF-receptor associated periodic syndromes (TRAPS).

The disclosed crystalline TNFR2 polypeptides, compositions, and/or combination therapies furthermore are useful for treating acute polyneuropathy; anorexia nervosa; Bell's palsy; chronic fatigue syndrome; transmissible dementia, including Creutzfeld-Jacob disease; demyelinating neuropathy; Guillain-Barre syndrome; vertebral disc disease; Gulf war syndrome; myasthenia gravis; silent cerebral ischemia; sleep disorders, including narcolepsy and sleep apnea; chronic neuronal degeneration; and stroke, including cerebral ischemic diseases.

Oncologic and Hematologic Disorders

Provided herein are methods for using crystalline TNFR2 polypeptiders, compositions, and/or combination therapies to treat various oncologic and hematologic disorders. For example, crystalline TNFR2 polypeptides are used to treat various forms of cancer, including acute myelogenous leukemia, Epstein-Barr virus-positive nasopharyngeal carcinoma, gall bladder carcinoma, glioma, colon, stomach, prostate, renal cell, cervical and ovarian cancers, lung cancer (SCLC and NSCLC), including cancer-associated nausea, cancer-associated cachexia, fatigue, asthenia, paraneoplastic syndrome of cachexia and hypercalcemia. Additional diseases treatable with the subject crystalline TNFR2 polypeptides, compositions, and/or combination therapies are solid tumors, including sarcoma, osteosarcoma, and carcinoma, such as adenocarcinoma (for example, breast cancer) and squamous cell carcinoma. In addition, the subject compounds, compositions, and/or combination therapies are useful for treating leukemia, including chronic or acute myelogenous leukemia, chronic or acute lymphoblastic leukemia, and hairy cell leukemia. Other malignancies with invasive metastatic potential can be treated with the subject compounds, compositions, and/or combination therapies, including multiple myeloma. When crystalline TNFR2 polypeptides are used to treat a tumor, this treatment may be administered in combination with antibodies targeted to membrane proteins that are expressed at a high level on the particular tumor being treated. For example, tumors such as breast, ovarian, and prostate carcinomas or other Her2-positive tumors, can be administered with crystalline TNFR2:Fc or other crystalline TNFR2 polypeptides in combination with antibodies against Her2/neu, such as HERCEPTIN® (known generically as "trastuzumab;" Genentech, Inc.). Cancer, for example ovarian cancer or prostate cancer, can be treated by concurrent administration of a crystalline TNFR2 polypeptide, such as crystalline TNFR2: Fc, and interferon-γ (Windbichler et al., 2000, *British J Cancer* 82: 1138-1144).

Various lymphoproliferative disorders also are treatable with the disclosed crystalline TNFR2 polypeptides, compositions, and/or combination therapies. These include, but are not limited to autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides) and Sézary syndrome.

In addition, the disclosed crystalline TNFR2 polypeptides, compositions, and/or combination therapies can be used to treat anemias and hematologic disorders, including anemia of chronic disease, aplastic anemia, including Fanconi's aplastic anemia; idiopathic thrombocytopenic purpura (ITP); myelodysplastic syndromes (including refractory anemia, refractory anemia with ringed sideroblasts, refractory anemia with excess blasts, refractory anemia with excess blasts in transformation); myelofibrosis/myeloid metaplasia; and sickle cell vasocclusive crisis. In addition, crystalline TNFR2 polypeptides, such as crystalline TNFR2: Fc, are useful for treating chronic idiopathic neutropenia.

A combination of a crystalline TNFR2 polypeptide and one or more anti-angiogenesis factors may be used to treat solid tumors, thereby reducing the vascularization that nourishes the tumor tissue. Suitable anti-angiogenic factors for such combination therapies include IL-8 inhibitors, angiostatin, endostatin, kringle 5, inhibitors of vascular endothelial growth factor (VEGF), angiopoietin-2 or other antagonists of angiopoietin-1, antagonists of platelet-activating factor, and antagonists of basic fibroblast growth factor. Antibodies against vascular endothelial growth factor, such as the recombinant humanized anti-VEGF (AVASTIN™, known generically as "bevacizumab;" Genentech, Inc.), are useful for combination treatments with crystalline TNFR2 polypeptides such as crystalline TNFR2:Fc.

In one embodiment of the invention, the crystalline TNFR2 polypeptide, such as crystalline TNFR2:Fc, is administered to cancer patients in combination with a proteasome inhibitor, including administration to patients suffering from hematologic cancers or solid tumors. The proteasome controls the stability of various proteins involved in the cell cycle and apoptosis, such as cyclins and NF-kappaB (see, for example, Schenkein, 2002, *Clin Lymphoma* 3: 49-55 and Adams, 2002, *Curr Opin Oncol* 14: 628-634). Proteasome inhibitors can induce apoptosis, and thus can sensitize cancer cells to other anti-cancer agents. Exemplary proteasome inhibitors for the subject combinations include, for example, carbobenzoxy-L-leucyl-L-leucyl-L-leucinal (MG132), clasto-lactacystin beta-lactone (A.G. Scientific, Inc.), carbobenzoxy-L-isoleucyl-(gamma)-t-butyl-L-glutamyl-L-alanyl-L-leucinal (PSI), N-acetyl-leu-leu-norleucinal (ALLN), MLN519 (Millennium Pharmaceuticals), [(1R)-3-methyl-1-[[(2S)-1-oxo-3-phenyl-2-[(pyrazinylcarbonyl)amino]propyl]-amino]butyl]boronic acid (PS-341, known generically as "bortezomib;" trade name VELCADE®; Millennium Pharmaceuticals), and carbobenzoxy-L-leucyl-L-leucyl-L-norvalinal (MG115; Affiniti Research Products). For example, multiple myeloma, ovarian cancer, prostate cancer, breast cancer, hematologic malignancies, such as lymphoma or leukemia, or other tumors may be treated concurrently with a proteasome inhibitor, such as PS-341, and a crystalline TNFR2 polypeptide, such as crystalline TNFR2:Fc or crystalline etanercept.

Undesired side effects of certain therapies can be treated with crystalline TNFR2 polypeptides, such as crystalline TNFR2:Fc. Such side effects in some instances are mediated by elevated TNF-alpha levels, thus such patients will benefit from treatment with an agent that reduces levels of TNF-alpha. For example, crystalline TNFR2 polypeptides such as crystalline TNFR2:Fc may be administered to help combat the nausea associated with chemotherapy or other drug-induced nausea. In addition, crystalline TNFR2 polypeptides are used to treat the radiation-induced brain damage associated with radiation treatment for brain tumors. Furthermore, crystalline TNFR2 polypeptides are used to treat the toxicity associated with the administration of monoclonal antibodies directed against antigens present on the surface of particular kinds of cancer cells. For example, the crystalline TNFR2 polypeptides disclosed herein may be used to treat toxicity associated with infusion of CAMPATH 1-H® (known generically as "alemtuzumab;" Berlex Laboratories; see also EP 0328404A1), which is used to treat chronic lymphocytic leukemia. CAMPATH 1-H is a humanized antibody specific for CD52, a cell surface antigen found on monocytes, B cells and T cells. In another embodiment of the invention, the disclosed crystalline TNFR2 polypeptides, such as crystalline TNFR2:Fc or crystalline etanercept, may be administered to ameliorate the autoimmune response disorder related to long-term interferon treatment.

A crystalline TNFR2 polypeptide can be administered to cancer patients to reduce the undesired side effects associated with long-term interferon administration, which can include fatigue, fever, neutropenia, rash, headache, digestive disorders, liver enzyme imbalances and so on. For example, interferon γ (IFNγ) has been shown to be active in ovarian cancer, thus a patient with ovarian cancer can be treated by concurrently administering IFNγ and a crystalline TNFR2 polypeptide, such as crystalline TNFR2:Fc, or crystalline etanercept. Similarly, IFNα is often used to treat melanoma, chronic myelogenous leukemia, basal cell carcinoma, hairy cell leukemia, bladder cancer, hemangiomas of infancy and childhood, multiple myeloma, Kaposi's sarcoma, mycosis fingoides, non-Hodgkin's lymphoma and renal cell carcinoma and can be administered concurrently with a crystalline TNFR2 polypeptide, such as crystalline TNFR2:Fc, to reduce interferon-induced side effects.

In addition, crystalline TNFR2 polypeptides can be used to prevent development of or alleviate drug resistance to agents that are bound by alpha-1-acid glycoprotein (AGP), a protein that capable of binding to small molecules and that preferentially binds to basic molecules. AGP is an acute phase protein that becomes increased in a variety of pathologic conditions, including chronic inflammation, myocardial infarction and cancer. STI 571 (Glivec®, generically known as "imatinib;" Novartis) is an active inhibitor of Bcr-Abl and C-kit kinase activity, and is useful for treating chronic myelogenous leukemia (CML). A mouse model study of CML has shown that AGP binds and inactivates imatinib, thus resulting in a resistance to this drug (Gambacorti-Passerini et al., 2000, *J Natl Can Inst* 92: 1641-1650). The level of AGP in a patient can be lowered by administering pentoxifylline (Voisin et al., 1998, *Am J Physiol* 275: R1412-R1419). The subject invention provides methods of preventing or reducing resistance to imatinib by concurrently administering a crystalline TNFR2 polypeptide, such as crystalline TNFR2:Fc or crystalline etanercept, to a CML patient who is undergoing treatment with imatinib. UCN-01 (7-hydroxystaurosporine), an agent used to treat gastrointestinal and other solid tumors, also has a propensity for binding to AGP (Senderowicz et al., 2000, *J Natl Cancer Inst* 92(5): 376-387); Noriaki et al., 2000, *Biol Pharmac Bull* 23(7): 893-895; Fuse et al., 1999, *Cancer Res* 59(5): 1054-1060; Tamura et al., 1999, *Proc Annu Meet Am Soc Clin Oncol* 18: A611). Provided herein is a method for preventing or reducing UCN-01 binding to AGP by administering a crystalline TNFR2 polypeptide, such as crystalline TNFR2:Fc, to a gastrointestinal cancer patient who is being treated concurrently with UCN-01, thereby enhancing the effectiveness of the UCN-01 treatment. Alternatively, patients receiving imatinib or UCN-01 can be treated by the concurrent administration of an IL-1 inhibitor or a crystalline TNFR2 polypeptide together with an IL-1 inhibitor, such as one of the IL-1 inhibitors described in WO 01/87328, which is hereby incorporated by reference in its entirety. For these methods, the crystalline TNFR2 polypeptide may be administered one or more times per week, for example, one, two or three times per week. One suitable mode of administration for the crystalline TNFR2 polypeptide is by subcutaneous injection. When the patient is an adult, suitable doses for injected crystalline TNFR2 polypeptide include 5-12 mg/m$^2$ of body surface area, or 25 mg or 50 mg per dose. If the patient is a pediatric patient, the crystalline TNFR2 polypeptide may be administered by subcutaneous injection one or more times per week at a dose of 0.4 mg/kg of body weight, up to a maximum of 25 mg per dose.

Pulmonary Disorders

A number of pulmonary disorders also can be treated with the disclosed crystalline TNFR2 polypeptides, compositions, and/or combination therapies. One such condition is adult respiratory distress syndrome (ARDS), which is associated with elevated TNF-alpha, and may be triggered by a variety of causes, including exposure to toxic chemicals, pancreatitis, trauma or other causes. The disclosed compounds, compositions, and/or combination therapies of the invention also are useful for treating broncho-pulmonary dysplasia (BPD); lymphangioleiomyomatosis; pulmonary hypertension; chronic fibrotic lung disease of preterm infants; and idiopathic bronchiectasis. Idiopathic bronchiectasis is a disease in which neutrophils mediate degradation of the proteoglycan component of the bronchial matrix. Proinflammatory mediators in the bronchial secretions of bronchiectasis patients, particularly TNF-alpha, are suspected of enhancing the degradative action of these neutrophils (Shum et al., *Am J Respir Crit Care Med* 162:1925-31 (2000)). The present invention provides treatment for idiopathic bronchiectasis that comprises administering a crystalline TNFR2 polypeptide, such as crystalline TNFR2:Fc. In addition, the compounds, compositions, and/or combination therapies of the invention are used to treat occupational lung diseases, including asbestosis, coal worker's pneumoconiosis, silicosis, or similar conditions associated with long-term exposure to fine particles. In other aspects of the invention, the disclosed compounds, compositions, and/or combination therapies are used to treat pulmonary disorders, including chronic obstructive pulmonary disease (COPD) associated with chronic bronchitis or emphysema; fibrotic lung diseases, such as cystic fibrosis, idiopathic pulmonary fibrosis and radiation-induced pulmonary fibrosis; sarcoidosis, including pulmonary sarcoidosis; and allergies, including allergic rhinitis, contact dermatitis, atopic dermatitis, and asthma.

Cystic fibrosis is an inherited condition characterized primarily by the accumulation of thick mucus, predisposing the patient to chronic lung infections and obstruction of the pancreas, which results in malabsorption of nutrients and malnutrition. Crystalline TNFR2 polypeptides may be administered to treat cystic fibrosis. If desired, treatment with crystalline TNFR2 polypeptides may be administered concurrently with corticosteroids, mucus-thinning agents such as inhaled recombinant deoxyribonuclease I (such as PULMOZYME®; Genentech, Inc.) or inhaled tobramycin (TOBI®; Pathogenesis, Inc.). Crystalline TNFR2 polypeptides also may be administered concurrently with corrective gene therapy, drugs that stimulate cystic fibrosis cells to secrete chloride, or other yet-to-be-discovered treatments. Sufficiency of treatment may be assessed, for example, by observing a decrease in the number of pathogenic organisms in sputum or lung lavage (such as *Haemophilus influenzae, Stapholococcus aureus*, and *Pseudomonas aeruginosa*), by monitoring the patient for weight gain, by detecting an increase in lung capacity, or by any other convenient means.

Crystalline TNFR2 polypeptides or crystalline TNFR2 polypeptides combined with the cytokine IFNγ-1b (such as ACTIMMUNE®; InterMune Pharmaceuticals) may be used for treating cystic fibrosis or fibrotic lung diseases, such as idiopathic pulmonary fibrosis, radiation-induced pulmonary fibrosis and bleomycin-induced pulmonary fibrosis. In addition, this combination is useful for treating other diseases characterized by organ fibrosis, including systemic sclerosis (also called "scleroderma"), which often involves fibrosis of the liver. For treating cystic fibrosis, crystalline TNFR2 polypeptide and IFNγ-1b may be combined with PULMOZYME® or TOBI® or other treatments for cystic fibrosis. Crystalline TNFR2 polypeptide alone or in combination with IFNγ-1b may be administered together with other treatments presently used for treating fibrotic lung disease. Such additional treatments include glucocorticoids, azathioprine, cyclophosphamide, penicillamine, colchisine, supplemental oxygen and so forth. Patients with fibrotic lung disease, such as IPF, often present with nonproductive cough, progressive dyspnea, and show a restrictive ventilatory pattern in pulmonary function tests. Chest radiographs reveal fibrotic accumulations in the patient's lungs. When treating fibrotic lung disease in accord with the disclosed methods, sufficiency of treatment may be detected by observing a decrease in the patient's coughing (when cough is present), or by using standard lung function tests to detect improvements in total lung capacity, vital capacity, residual lung volume, or by administering a arterial blood gas determination measuring desaturation under exercising conditions, and showing that the patient's lung function has improved according to one or more of these measures. In addition, patient improvement may be determined through chest radiography results showing that the progression of fibrosis in the patient's lungs has become arrested or reduced. In addition, crystalline TNFR2 polypeptides are useful for treating organ fibrosis when administered in combination with relaxin, a hormone that down-regulates collagen production thus inhibiting fibrosis, or when given in combination with agents that block the fibrogenic activity of TGF-β. Combination therapies using crystalline TNFR2 polypeptide and recombinant human relaxin are useful, for example, for treating systemic sclerosis or fibrotic lung diseases, including cystic fibrosis, idiopathic pulmonary fibrosis, radiation-induced pulmonary fibrosis, and bleomycin-induced pulmonary fibrosis.

Rheumatic and Skin Disorders

Other embodiments provide methods for using the disclosed crystalline TNFR2 polypeptides, compositions, and/or combination therapies to treat a variety of rheumatic disorders. The use of TNF-alpha inhibitors in treating rheumatoid arthritis is reviewed in Moreland, L. W., 1991, *J Rheumatol* 26 Suppl 57: 7-15, and the use of TNF-alpha inhibitors in treading spondylo-arthropathy and ankylosing spondylitis is disclosed in Schnarr et al., 2002, *Clin Exp Rheumatol* 20 (Suppl. 28): S126-S129 and in Gorman et al., 2002, *N Engl J Med* 346 (18): 1349-1356, respectively. Conditions that can be treated with crystalline TNFR2 polypeptides, compositions, and/or combination therapies include: adult and juvenile rheumatoid arthritis; systemic lupus erythematosus; gout; osteoarthritis; polymyalgia rheumatica; seronegative spondylarthropathies, including ankylosing spondylitis; and Reiter's disease (reactive arthritis). The subject crystalline TNFR2 polypeptides, compositions, and/or combination therapies are used also to treat psoriatic arthritis and chronic Lyme arthritis; the use of TNF-alpha inhibitors in treating psoriatic arthritis is described in Rudermam, E. M., 2002, *Am J Manag Care* 8: S171-S180 and in Salvarani et al., 2002, Clin Exp Rheumatol 20 (Suppl. 28): S71-S75. Also treatable with these compounds, compositions, and/or combination therapies are Still's disease and uveitis associated with rheumatoid arthritis. In addition, the compounds, compositions, and/or combination therapies of the invention are used in treating disorders resulting in inflammation of the voluntary muscle, including dermatomyositis and polymyositis. Moreover, the compounds, compositions, and/or combinations disclosed herein are useful for treating sporadic inclusion body myositis, as TNF-alpha may play a significant role in the progression of this muscle disease. In addition, the compounds, compositions, and/or combinations disclosed herein are used to treat multicentric reticulohistiocytosis, a disease in which joint destruction and papular nodules of the face and hands are associated with excess production of proinflammatory cytokines by multinucleated giant cells. The crystalline TNFR2 polypeptides, compositions, and/or combination therapies of the invention may be used to inhibit hypertrophic scarring, a phenomenon believed to result in part from excessive TNF-alpha secretion. Crystalline TNFR2 polypeptides may be administered alone or concurrently with other agents that inhibit hypertrophic scarring, such as inhibitors of TGF-alpha.

Disorders involving the skin or mucous membranes also are treatable using the disclosed crystalline TNFR2 polypeptides, compositions, and/or combination therapies. Such disorders include acantholytic diseases, including Darier's disease, keratosis follicularis, and pemphigus vulgaris. Also treatable with the subject crystalline TNFR2 polypeptides, compositions, and/or combination therapies are acne; acne rosacea; alopecia greata; aphthous stomatitis; bullous pemphigoid; bums; dermatitis herpetiformis; eczema; erythema, including erythema multiforme and erythema multiforme bullosum (Stevens-Johnson syndrome); inflammatory skin disease; lichen planus; linear IgA bullous disease (chronic bullous dermatosis of childhood); loss of skin elasticity; mucosal surface ulcers; neutrophilic dermatitis (Sweet's syndrome); pityriasis rubra pilaris; psoriasis; pyoderma gangrenosum; and toxic epidermal necrolysis.

In another embodiment, the disclosed crystalline TNFR2 polypeptides are used to treat and prevent the recurrence of lipodermatosclerosis and chronic venous ulcers, which most often are located on the legs. Studies have shown that TNF-alpha may contribute to the pathogenesis of lipodermatosclerosis and chronic venous ulcers by activation of matrix metalloproteinase 2 (MMP2), and by inducing the production of TGFα and other cytokines. Oxpentifylline and pentoxifylline have been shown to be effective in this setting. The disclosed crystalline TNFR2 polypeptides, including crystalline TNFR2:Fc or crystalline etanercept, may be used to treat chronic venous ulcers either alone or in combination with one or more of oxpentifylline, pentoxifylline, GM-CSF, leptin, PDGF, bFGF, EGF, TGF, and/or IGF. These treatments will accelerate healing and prevent recurrences. Administration may be systemic or local. For local administration, the crystalline TNFR2 polypeptide is applied topically in an ointment, lotion, gel or cream, or is injected perilesionally directly into or within about ten centimeters of the ulcer.

Additional Disorders

Provided also are methods for using crystalline TNFR2 polypeptides, compositions, and/or combination therapies to treat various disorders of the endocrine system. For example, the crystalline TNFR2 polypeptides are used to treat juvenile onset diabetes (includes autoimmune and insulin-dependent types of diabetes) and also to treat maturity onset diabetes (includes non-insulin dependent and obesity-mediated diabetes). In addition, the subject compounds, compositions, and/or combination therapies are used to treat secondary conditions associated with diabetes, such as diabetic retinopathy, kidney transplant rejection in diabetic patients, obesity-mediated insulin resistance, and renal failure, which itself may be associated with proteinurea and hypertension. Other endocrine disorders also are treatable with these compounds, compositions, and/or combination therapies, including polycystic ovarian disease, X-linked adrenoleukodystrophy, hypothyroidism, and thyroiditis, including Hashimoto's thyroiditis (i.e., autoimmune thyroiditis).

The disclosed crystalline TNFR2 polypeptides, such as crystalline TNFR2:Fc, compositions, and/or combination therapies are further used to treat conditions of the liver such as hepatitis, including acute alcoholic hepatitis, acute drug-induced or viral hepatitis, hepatitis A, B and C, sclerosing cholangitis, autoimmune hepatitis, idiopathic portal hypertension, and inflammation of the liver due to unknown causes. The foregoing liver diseases may be treated with a crystalline TNFR2 polypeptide, such as crystalline TNFR2:Fc, concurrently with other medications used to treat the same conditions. As an example, crystalline TNFR2 polypeptides may be used to treat hepatitis C, including chronic hepatitis C, in patients who are concurrently treated with interferon-alpha (IFNalpha). High expression of TNF-alpha in the liver interferes with the action of IFNalpha, thus interfering with the patient's response to IFNalpha treatment (Hong et al., 2001, *FASEB J* 15: 1595-1597). Treatments that may be administered concurrently with crystalline TNFR2 polypeptides to treat hepatitis C include pegylated IFNalpha, ribavirin, or a combination of ribavirin and interferon-alpha or pegylated interferon-alpha. Interferon-alpha moieties suitable for concurrent use with crystalline TNFR2 polypeptides include IFNalpha-2a (such as ROFERON®; Hoffmann-LaRoche), pegylated IFNalpha-2a (such as PEGASYS®; Hoffmann-LaRoche), pegylated IFNalpha-2a or -2b as described in US20020127203A1, or the pegylated-IFNalpha conjugates described in WO 9964016. In another embodiment, Hepatitis C can be treated by concurrent administration of interferon-alpha and a crystalline TNFR2 polypeptide other than crystalline TNFR2:Fc, such as crystalline forms of lenercept or onercept.

Conditions of the gastrointestinal system also are treatable with crystalline TNFR2 polypeptides, compositions, and/or combination therapies, including coeliac disease; the use of TNF-alpha inhibitors in treating Crohn's disease is disclosed in Ricart et al., 2002, *Drugs of Today* 38 (11): 725-744. In addition, the compounds, compositions, and/or combination therapies of the invention are used to treat Crohn's disease; nausea associated with gastrointestinal disorders or other systemic disorders; ulcerative colitis; idiopathic gastroparesis; cholelithiasis (gallstones); pancreatitis, including chronic pancreatitis and lung injury associated with acute pancreatitis; and ulcers, including gastric and duodenal ulcers.

Included also are methods for using the subject crystalline TNFR2 polypeptides, compositions, and/or combination therapies for treating disorders of the genitourinary system, such as glomerulonephritis, including autoimmune glomerulonephritis, glomerulonephritis due to exposure to toxins or glomerulonephritis secondary to infections with haemolytic streptococci or other infectious agents. Also treatable with the compounds, compositions, and/or combination therapies of the invention are uremic syndrome and its clinical complications (for example, renal failure, anemia, and hypertrophic cardiomyopathy), including uremic syndrome associated with exposure to environmental toxins, drugs, or other causes. Further conditions treatable with the compounds, compositions, and/or combination therapies of the invention are complications of hemodialysis; prostate conditions, including benign prostatic hypertrophy, nonbacterial prostatitis and chronic prostatitis; and complications of hemodialysis.

In addition, the disclosed crystalline TNFR2 polypeptides, compositions, and/or combination therapies are used to treat various disorders that involve hearing loss such as those that are associated with abnormal TNF-alpha expression. One of these is inner ear or cochlear nerve-associated hearing loss that is thought to result from an autoimmune process, i.e., autoimmune hearing loss. This condition currently is treated with steroids, methotrexate and/or cyclophosphamide, which may be administered concurrently with crystalline TNFR2:Fc or other crystalline TNFR2 polypeptide. Also treatable with the disclosed crystalline TNFR2 polypeptides, compositions, and/or combination therapies is cholesteatoma, a middle ear disorder often associated with hearing loss.

In addition, the subject invention provides crystalline TNFR2 polypeptides, compositions, and/or combination therapies for the treatment of non-arthritic medical conditions of the bones and joints. This encompasses osteoclast disorders that lead to bone loss, such as but not limited to osteoporosis, including post-menopausal osteoporosis, periodontitis resulting in tooth loosening or loss, and prosthesis loosening after joint replacement (generally associated with an inflammatory response to wear debris). This latter condition also is called "orthopedic implant osteolysis." Other conditions treatable by administering crystalline TNFR2 polypeptides, such as crystalline TNFR2:Fc, include temporal mandibular joint dysfunction (TMJ) and bone loss due to the hypercalcemia of cancer, including metastases to bone, such as, for example, may occur in melanoma or carcinoma of lung, breast, lung, squamous cell carcinoma, head and neck cancer, renal cancer, or prostate cancer.

Disorders associated with transplantation also are treatable with the disclosed crystalline TNFR2 polypeptides, compositions, and/or combination therapies, such as graft-versus-host disease, and other complications resulting from solid organ transplantation, including transplantation of heart, liver, lung, skin, kidney or other organs. Such crystalline TNFR2 polypeptides may be administered, for example, to prevent or inhibit the development of bronchiolitis obliterans, such as bronchiolitis obliterans after lung transplantation and bronchiolitis obliterans organizing pneumonia. Patients undergoing autologous hematopoietic stem cell transplantation in the form of peripheral blood stem cell transplantation may develop "engraftment syndrome," or "ES," which is an adverse and generally self-limited response that occurs about the time of hematopoietic engraftment and which can result in pulmonary deterioration. ES may be treated with inhibitors of either IL-8 or TNF-alpha (such as crystalline TNFR2:Fc or other crystalline TNFR2 polypeptides), or with a combination of inhibitors against both of these cytokines. The disclosed crystalline TNFR2 polypeptides also are useful for treating or preventing graft failure, such as bone marrow graft rejection or failure of the recipient's body to accept other types of grafts, such as corneal transplants, or such as liver or other solid organ transplants, in which graft rejection is often accompanied by elevated levels of TNF-alpha and IL-10.

Graft rejection may be treated with a combination of a crystalline TNFR2 polypeptide and an IL-10 inhibitor.

Ocular disorders also are treatable with the disclosed crystalline TNFR2 polypeptides, compositions, and/or combination therapies, including rhegmatogenous retinal detachment, and inflammatory eye disease, and inflammatory eye disease associated with smoking as well as macular degeneration associated with smoking or associated with aging.

Crystalline TNFR2 polypeptides such as crystalline TNFR2:Fc, the disclosed compositions, and/or combination therapies described herein are useful for treating disorders that affect the female reproductive system. Examples include, but are not limited to, multiple implant failure/infertility; fetal loss syndrome or IV embryo loss (spontaneous abortion); preeclamptic pregnancies or eclampsia; and endometriosis.

In addition, the disclosed crystalline TNFR2 polypeptides, compositions, and/or combination therapies are useful for treating obesity, including treatment to bring about a decrease in leptin formation, or weight gain associated with the use of anti-depressant medications. Also, the compounds, compositions, and/or combination therapies of the invention are used to treat neurogenic pain, sciatica, symptoms of aging, severe drug reactions (for example, Il-2 toxicity or bleomycin-induced pneumopathy and fibrosis), or to suppress the inflammatory response prior, during, or after the transfusion of allogeneic red blood cells in cardiac or other surgery, or in treating a traumatic injury to a limb or joint, such as traumatic knee injury. Various other medical disorders treatable with the disclosed crystalline TNFR2 polypeptides, compositions, and/or combination therapies include; multiple sclerosis; Behcet's syndrome; Sjogren's syndrome; autoimmune hemolytic anemia; beta thalassemia; amyotrophic lateral sclerosis (Lou Gehrig's Disease); Parkinson's disease; and tenosynovitis of unknown cause, as well as various autoimmune disorders or diseases associated with hereditary deficiencies. In addition, the subject crystalline TNFR2 polypeptides, compositions, and/or combination therapies are used to treat hereditary conditions such as Gaucher's disease, Huntington's disease, linear IgA disease, and muscular dystrophy.

In yet another embodiment of the invention, the crystalline TNFR2 polypeptides disclosed herein are used to treat autism spectrum disorder and other pervasive developmental disorders. It has been shown that proinflammatory cytokines, including TNF-alpha and IL-1 are overproduced in a subset of autistic patients, indicating that these patients had excessive innate immune responses and/or aberrant production of regulatory cytokines for T cell responses. Thus, provided herein are methods for treating autism spectrum disorder by administering a crystalline TNFR2 polypeptide such as crystalline TNFR2:Fc.

Additional Combination Therapies

Various other medicaments used to treat the diseases described herein may also be administered concurrently with compositions comprising crystalline TNFR2, or compositions prepared using crystalline TNFR2. Such medicaments include: antivirals; antibiotics; analgesics; non-steroidal anti-inflammatory drugs (NSAIDs); disease-modifying anti-rheumatic drugs (DMARDs); corticosteroids; topical steroids; systemic steroids (e.g., prednisone); cytokines; antagonists of inflammatory cytokines; antibodies against T cell surface proteins; oral retinoids; salicylic acid; and hydroxyurea. Suitable analgesics for such combinations include: acetaminophen, codeine, propoxyphene napsylate, oxycodone hydrochloride, hydrocodone bitartrate, and tramadol. NSAIDs suitable for the subject combination treatments include: salicylic acid (aspirin) and salicylate derivatives; ibuprofen; indomethacin; celecoxib (CELEBREX®); rofecoxib (VIOXX®); valdecoxib (BEXTRA®); ketorolac; nambumetone; piroxicam; naproxen; oxaprozin; sulindac; ketoprofen; diclofenac; and other COX-1 and COX-2 inhibitors, propionic acid derivatives, acetic acid derivatives, fumaric acid derivatives, carboxylic acid derivatives, butyric acid derivatives, oxicams, pyrazoles and pyrazolones, including newly developed anti-inflammatories. DMARDs suitable for such combinations include: azathioprine, cyclophosphamide, cyclosporine, hydroxychloroquine sulfate, methotrexate, leflunomide, minocycline, penicillamine, sulfasalazine, and gold compounds such as oral gold, gold sodium thiomalate, and aurothioglucose. Examples of cytokine inhibitors that can be used in combination with crystalline TNFR2 include, for example, antagonists of TGFβ, of IL-6, or of IL-8. crystalline TNFR2 polypeptides also may be administered in combination with the cytokines GM-CSF, IL-2, and/or inhibitors of protein kinase A type I to enhance T cell proliferation in HIV-infected patients who are receiving anti-retroviral therapy. In addition, crystalline TNFR2 polypeptides may be combined with inhibitors of IL-13 to treat Hodgkin's disease. Nerve growth factors also can be combined with crystalline TNFR2 polypeptidess to treat certain conditions. Such conditions include neurodegenerative diseases, spinal cord injury and multiple sclerosis. Other conditions treatable with this combination are glaucoma and diabetes. In addition, the crystalline TNFR2 polypeptides may be administered in combination with antimalarials or colchicine.

Other compounds suitable for treating the diseases described herein in combination with crystalline TNFR2 polypeptides include small molecules such as thalidomide or thalidomide analogs, pentoxifylline, or matrix metalloproteinase (MMP) inhibitors or other small molecules. Suitable MMP inhibitors for this purpose include, for example, those described in U.S. Pat. Nos. 5,883,131, 5,863,949, and 5,861,510 as well as the mercapto alkyl peptidyl compounds described in U.S. Pat. No. 5,872,146. Other small molecules capable of reducing TNF-alpha production, include, for example, the molecules described in U.S. Pat. Nos. 5,508,300, 5,596,013, and 5,563,143, any of which can be administered in combination with crystalline TNFR2 polypeptides. Additional small molecules useful in combination with crystalline TNFR2 polypeptides for treating the diseases described herein include the MMP inhibitors that are described in U.S. Pat. No. 5,747,514, U.S. Pat. No. 5,691,382, as well as the hydroxamic acid derivatives described in U.S. Pat. No. 5,821,262. The diseases described herein also may be treated with combination therapies including small molecules that inhibit phosphodiesterase IV and TNF-alpha production, such as substituted oxime derivatives (WO 96/00215), quinoline sulfonamides (U.S. Pat. No. 5,834,485), aryl furan derivatives (WO 99/18095) and heterobicyclic derivatives (WO 96/01825; GB 2 291 422 A). Also useful in combination with crystalline TNFR2 polypeptides are thiazole derivatives that suppress TNF-alpha and IFNγ (WO 99/15524), as well as xanthine derivatives that suppress TNF-alpha and other proinflammatory cytokines (see, for example, U.S. Pat. No. 5,118,500, U.S. Pat. No. 5,096,906, and U.S. Pat. No. 5,196,430). Additional small molecules useful for treating the hereindescribed conditions concurrently with crystalline TNFR2 polypeptides include those disclosed in U.S. Pat. No. 5,547,979.

Additionally, crystalline TNFR2 polypeptides may be combined with a second TNF-alpha antagonist, including an antibody against TNF-alpha or TNF-alpha receptors, a TNF-alpha-derived peptide that acts as a competitive inhibitor of TNF-alpha (such as those described in U.S. Pat. No. 5,795,859 or U.S. Pat. No. 6,107,273), a soluble TNFR other than an Ig fusion protein, or other molecules that reduce endogenous TNF-alpha levels, such as antisense oligonucleotides or ribozymes that inhibit TNF-alpha production or inhibitors of the TNF-alpha converting enzyme (see e.g., U.S. Pat. No. 5,594,106), or any of the small molecules or TNF-alpha inhibitors that are described above, including pentoxifylline or thalidomide or derivatives thereof. Thalidomide or thalidomide derivatives may be administered concurrently with crystalline TNFR2 polypeptides to treat, for example, hematologic and oncologic disorders. Examples of such disorders, any of which may be treated with crystalline TNFR2 polypeptides alone, include graft-versus-host disease, myelodysplastic syndromes, aplastic anemia, sickle cell vasocclusive crisis, acute myelogenous leukemia (AML), chronic lymphocytic leukemia (CLL), hairy cell leukemia, paraneoplastic syndrome of cachexia and hypercalcemia, multiple myeloma and POEMS syndrome (polyneuropathy, organomegaly, endocrinopathy, monoclonal gammopathy, and skin changes), myelofibrosis/myeloid metaplasia, Kaposi's sarcoma, cachexia associated with cancer, amyloidosis, anemia of chronic disease, squamous cell carcinoma, idiopathic thrombocytopenic purpura (ITP), thrombotic thrombocytopenic purpura (TTP), autoimmune hemolytic anemia, and beta thalassemia. In one embodiment of the invention, the crystalline TNFR2 polypeptide used in combination with thalidomide is crystalline TNFR2:Fc or crystalline etanercept.

In addition, the subject invention provides methods for treating a human patient in need thereof, the method involving administering to the patient a therapeutically effective amount of a crystalline TNFR2 polypeptide and an IL-4 inhibitor, as described in US 2001/0021380 A1, which is incorporated by reference in its entirety herein. Conditions effectively treated by a combination of a crystalline TNFR2 polypeptide and an IL-4 inhibitor include asthma, chronic obstructive pulmonary disease, pulmonary alveolar proteinosis, bleomycin-induced pneumopathy and fibrosis, radiation-induced pulmonary fibrosis, cystic fibrosis, collagen accumulation in the lungs, ARDS; various skin disorders, including but not limited to dermatitis herpetiformis (Duhring's disease), atopic dermatitis, contact dermatitis, urticaria (including chronic idiopathic urticaria), and autoimmune blistering diseases, including pemphigus vulgaris and bullous pemphigoid; myasthenia gravis, sarcoidosis, including pulmonary sarcoidosis, scleroderma, reactive arthritis, hyper IgE syndrome, multiple sclerosis, and idiopathic hypereosinophil syndrome; allergic reactions to medication, and as an adjuvant to allergy immunotherapy. In certain embodiments, combinations of crystalline TNFR2 polypeptides and IL-4 inhibitors are administered one or more times per week by subcutaneous injection or by aerosol pulmonary administration, for example by nebulizer.

Other treatments for the hereindescribed diseases include administering crystalline TNFR2 polypeptides concurrently with compounds that block the binding of RANK and RANK-ligand, such as antagonistic antibodies against RANK or RANK-ligand, osteoprotegerin or soluble forms of RANK, including RANK:Fc, and soluble forms of RANK-ligand that do not trigger RANK. In one embodiment of the invention, antibodies that specifically bind human RANKL are administered concurrently with crystalline TNFR2 polypeptide, such as crystalline TNFR2:Fc. Soluble forms of RANK suitable for these combinations are described, for example, in U.S. Pat. No. 6,017,729. The concurrent administration of crystalline TNFR2 polypeptides together with RANK:Fc or osteoprotegerin is useful for preventing bone destruction in various settings including but not limited to osteoporosis, multiple myeloma or other malignancies that cause bone degeneration, or anti-tumor therapy aimed at preventing metastasis to bone, or bone destruction associated with prosthesis wear debris or with periodontitis. Tumors that are treatable with a combination of a crystalline TNFR2 polypeptide and a RANK inhibitor include breast cancer, lung cancer, melanoma, bone cancer, squamous cell carcinoma, head and neck cancer, renal cancer, prostate cancer, and cancers associated with hypercalcemia.

Additional Uses

Transfection of lymphocytes with non-viral vectors can lead to apoptosis of the target cells through a TNF-alpha and CD95-mediated pathway (see, for example, Ebert et al., *Cytokines, Cell & Mol Ther* 5:165-73 (1999)). Crystalline TNFR2 polypeptides, such as crystalline TNFR2:Fc, may be used alone or in combination with a CD95 inhibitor, such as an antibody against CD95, to inhibit this apoptosis. This treatment will augment gene transfer to lymphocytes when non-viral vectors are used, particularly when liposome-mediated or receptor-mediated gene transfer methods are used. Such treatment will improve the incorporation of the exogenous gene into the target cells.

In addition, the present compositions may also be used for manufacture of one or more medicaments for treatment or amelioration of the conditions the crystalline TNFR2 polypeptide is intended to treat.

The following examples are offered to more fully illustrate the invention, but are not to be construed as limiting the scope thereof.

EXAMPLE 1

Method for the Crystallization of ENBREL® (Etanercept)

Etanercept polypeptide consists of a portion of the extracellular domain of human tumor necrosis factor receptor 2 (TNFR p75) fused to a portion of human immunoglobulin G1 (IgG1), as described above. Etanercept polypeptide was prepared by expressing DNA construct encoding etanercept in mammalian host cells and then was purified to substantial homogeneity. For the following crystallization experiments, the etanercept polypeptide was suspended in a phosphate buffer.

Crystallization of etanercept was achieved using a crystallization screen (PEG/LiCl Grid Screen; Hampton Research, Aliso Viejo, Calif.), which employs a method for crystallization of macromolecules known as 'hanging drop' vapor diffusion. A drop composed of a mixture of the polypeptide sample and the crystallization reagent (the "crystallization buffer" or the "mother liquor") is deposited on the underside of a sialanized coverslip, and then the drop on the coverslip is sealed with grease and placed over typically a 24 well VDX tray causing a vapor equilibrium with a liquid reservoir of reagent. To achieve equilibrium, water vapor exchanges between the drop and a one milliliter reservoir solution in the well of the tray. As water leaves the drop, the polypeptide sample undergoes an increase in relative concentration which may eventually lead to supersaturation. It is the increased concentration of the polypeptide sample that is required for crystallization to take place. Typically the drop contains a lower concentration of reagent than the reservoir, and typically, the drop contained half the concentration of reagent in the reservoir, because equal volumes of sample and reagent were mixed to form the drop. In these experiments, the initial polypeptide concentration in the drop was usually 25.48 mg/mL or 50.96 mg/mL, but crystallization was also observed at etanercept polypeptide concentrations of approximately 6 mg/mL and may be obtained at higher concentrations such as 100 mg/mL, or at lower concentrations of polypeptide such as approximately 3 mg/mL, but at lower concentrations, incubation for longer times may be required for crystal growth, depending on the size of the initial drop.

The crystallization screen was set up in 24-well VDX polypropylene tissue culture trays. Each position in the VDX tray contained 1 mL of reagent reservoir, with the reagent reservoir in each well differing in composition from that in the other wells, to establish an array of differing crystallization buffer conditions. One microliter of polypeptide solution at each polypeptide concentration was added to 1 microliter of reservoir solution to form the drops. Trays were incubated either at 5±3 degrees C. or at ambient room temperature (20±3 degrees C.). Crystals appeared in approximately 48 hours in some of the wells incubated at ambient room temperature, and continued to grow over subsequent days.

In the initial screens, crystals were obtained in the following conditions, using either an etanercept concentration of 25.48 mg/mL or a concentration of 50.96 mg/mL:

1. 1.0M lithium chloride, 0.1M HEPES pH 7.0; 30% polyethylene glycol 6000
2. 1.0M lithium chloride, 0.1M Tris-HCl pH 8.0; 30% polyethylene glycol 6000
3. 1.0M lithium chloride, 0.1M Bicine pH 9.0; 30% polyethylene glycol 6000
4. 0.2M lithium sulfate, 0.1M Tris-HCl pH 8.5, 30% polyethylene glycol 4000
5. 0.2M lithium sulfate, 0.1M Tris-HCl pH 8.5, 25% polyethylene glycol 3350
6. 0.5M lithium sulfate, 0.1M Tris-HCl pH 8.5

The etanercept crystals formed under the first three conditions above were rods or rod clusters approximately 1 mm in length, and were often accompanied by an amorphous precipitant. The etanercept crystals formed in the lithium sulfate conditions were rods approximately 0.1-0.2 mm in length, and were produced without the amorphous precipitate seen in the lithium chloride conditions. Some of the etanercept crystals were tested by X-ray diffraction and did not show a salt-like diffraction pattern, a result consistent with the crystals containing polypeptide material. Some of the etanercept crystals were solublized and their polypeptide content was partially sequenced by seven cycles of automated Edman degradation; a 3-4 pmol partial amino acid sequence was obtained from these crystals and was confirmed to match the N-terminal portion of the etanercept sequence (LPAQVAF; see amino acids 1 through 7 of SEQ ID NO:4). FIG. 1 is a photograph of etanercept crystals formed from a polypeptide solution containing 50.96 mg of etanercept per milliliter, with a crystallization reservoir buffer of 0.1M HEPES pH 7.0, 30% PEG 6000, 0.7M lithium chloride; after seven days at ambient room temperature the crystals were harvested manually, extensively washed in the above reservoir buffer, and the photograph was taken. Crystals from this group were submitted for the N-terminal amino acid sequence analysis described above. Another crystallization condition—1M lithium sulfate, O. 1M Tris-HCl pH 8.5, 0.01M nickel chloride-produced crystals; however, the polypeptide content of these crystals was not confirmed and therefore under this particular combination of conditions salt crystals are thought to have formed.

Based on these results, each of the three parameters of the first three conditions above (LiCl concentration, pH, and polyethylene glycol (PEG) 6000 concentration expressed as % (weight/volume)) was varied in additional experiments, which resulted in crystals forming in every drop in the additional experimental trays. Lithium chloride concentrations between 0.7M and 1.2M, PEG 6000 concentrations between 22% and 32%, and 0.1M HEPES pH values between pH 6.8 and 7.3 all resulted in successful crystallization in approximately 48 hours at ambient room temperature, at etanercept concentrations of 25.48 and 50.96 mg/mL. Further experiments expanded the range of successful crystallization conditions to include 0.2M through 1.2M LiCl, and 16% through 32% PEG 6000, although crystallization of etanercept may not occur at every combination of conditions which includes 0.2M LiCl, and/or etanercept crystals may take longer to form when 0.2M LiCl is used. Therefore, all combinations of the following conditions —lithium chloride concentrations between 0.3M and 1.2M, PEG 6000 concentrations between 16% and 32%, and 0.1M HEPES pH values between pH 6.8 and 7.3—are considered to be suitable conditions for crystallization of etanercept. In addition, conditions containing between 0.2M and 0.5M lithium sulfate, 0.1M Tris-HCl at approximately pH 8.5, and optionally including up to 30% PEG in the size range of PEG 3350-PEG 4000, are considered to be suitable conditions for crystallization of etanercept.

EXAMPLE 2

Additional Methods for the Crystallization of ENBREL® (Etanercept)

The "hanging-drop" method of crystallization, as described in Example 1 above, was used to prepare additional crystals of etanercept. Etanercept was reconstituted from commercially available ENBREL® lyophilized powder as per product instructions: a vial of ENBREL® lyophilized powder contains 25 mg etanercept, 40 mg mannitol, 10 mg sucrose, and 1.2 mg tromethamine, which is reconstituted with 1 mL of Sterile Bacteriostatic Water for Injection, USP (containing 0.9% benzyl alcohol). The reconstituted etanercept solution was dialyzed into water using a 10,000 molecular weight cut off dialysis cassette, and then concentrated to 100 mg/mL using a 10,000 molecular weight cut off centrifugal filter. Each crystallization well contained 1.0 mL of a particular crystallization reagent, as listed below, in the reservoir. Drops were made by adding 1 microliter of the 100 mg/mL solution of etanercept to 1 microliter of that crystallization reagent. Crystals were grown at ambient room temperature (approximately 22 degrees C.); needle-like crystals of etanercept about 100 micrometers in length formed in all of the crystallization reagents listed below, in some cases in as few as two days, and in other cases over a period of two to four weeks.

| Salt Condition: | Buffer Condition: | 2-methyl-2,4-pentanediol (MPD) Condition: |
|---|---|---|
| 0.09 M ammonium phosphate | 0.10 M sodium acetate, pH 4.5 | 40.28% MPD |
| 0.10 M ammonium phosphate | 0.10 M sodium acetate, pH 4.0 | 37.82% MPD |
| 0.10 M ammonium phosphate | 0.10 M sodium acetate, pH 5.0 | 35.11% MPD |
| 0.08 M ammonium phosphate | 0.10 M sodium acetate, pH 5.0 | 41.83% MPD |
| 0.12 M ammonium phosphate | 0.10 M sodium acetate, pH 4.0 | 31.30% MPD |
| 0.15 M ammonium phosphate | 0.10 M sodium acetate, pH 5.0 | 43.82% MPD |
| 0.11 M ammonium phosphate | 0.10 M sodium acetate, pH 4.0 | 30.55% MPD |
| 0.04 M ammonium phosphate | 0.10 M sodium acetate, pH 5.0 | 45.75% MPD |
| 0.19 M ammonium phosphate | 0.10 M sodium acetate, pH 4.0 | 30.78% MPD |
| 0.14 M ammonium phosphate | 0.10 M sodium acetate, pH 4.0 | 37.13% MPD |
| 0.16 M ammonium phosphate | 0.10 M sodium acetate, pH 4.0 | 31.27% MPD |
| 0.23 M ammonium phosphate | 0.10 M sodium acetate, pH 4.0 | 41.87% MPD |
| 0.18 M ammonium phosphate | 0.10 M sodium acetate, pH 4.5 | 34.10% MPD |
| 0.09 M ammonium phosphate | 0.10 M sodium acetate, pH 4.0 | 46.00% MPD |
| 0.09 M ammonium phosphate | 0.10 M sodium acetate, pH 4.5 | 46.01% MPD |
| 0.09 M ammonium phosphate | 0.10 M Hepes, pH 7.5 | 33.92% MPD |
| 0.20 M ammonium phosphate | 0.10 M Tris, pH 8.5 | 50.0% MPD |

In additional crystallization experiments, needle-like crystals of etanercept about 100 micrometers in length formed over a period of two to four weeks under the following crystallization conditions:

| Salt Condition: | Buffer Condition: | PEG Condition: | Temperature: |
|---|---|---|---|
| 1.0 M di-ammonium hydrogen phosphate; 0.2 M sodium chloride | 0.1 M imidazole, pH 8.0 | — | approximately 22 degrees C. |
| 1.0 M di-ammonium hydrogen phosphate 0.2 M sodium chloride | 0.1 M imidazole, pH 8.0 | — | approximately 22 degrees C. |
| | 0.1 M CAPS (3-[cyclohexylamino]-1-propanesulfonic acid), pH 10.5 | 20% PEG 8000 | 2-8 degrees C. |

EXAMPLE 3

Further Expansion of Crystallization Conditions

Vapor-diffusion crystallization methods, such as the "hanging drop" method described for crystallization of etanercept in Example 1 above, can be varied in order to achieve crystallization of polypeptides such as TNFR2 polypeptides. For example, other volumes of polypeptide sample relative to reagent can be mixed to vary the difference in reagent concentration between the drop and the reservoir, and also the initial polypeptide concentration in the drop. Mixing one part reagent to nine parts polypeptide sample would produce a drop with an initial concentration of reagent that is 0.1 times that of the reagent concentration of the reservoir. In certain embodiments of the invention, the initial concentration of crystallization reagent in the drop is approximately 0.05, 0.1, 0.2, 0.3, 0.4, 0.45, 0.5, 0.55, 0.6, 0.7, 0.8, 0.85, 0.9, or 0.95 times that of the concentration of crystallization reagent in the reservoir. The initial polypeptide concentration in the drop can be at least as low as approximately 6 mg/mL and at least as high as 100 mg/mL and possibly as high as 120 mg/mL; lower concentrations of polypeptide such as 3 mg/mL may form crystals, but can require longer incubation times before crystals can be detected.

Further expansion of the crystallization conditions may yield additional conditions that are appropriate for obtaining crystals of etanercept or other TNFR2 polypeptides, as described below. For example, combinations can be made of a salt condition, a pH buffer condition, an optional PEG condition, and an optional cofactor condition, wherein each condition is selected from the corresponding group of conditions described below.

| | Value Ranges; Minimum (selected from below) to Maximum (selected from below) | | |
|---|---|---|---|
| | Minimum Values: | Maximum Values: | Examples of Specific Values: |
| Salt conditions: | | | |
| Lithium chloride | 0.05 M or 0.1 M | 1.5 M, 2.0 M, or 5.0 M | 0.5 M, 0.7 M, 1.0 M, 1.2 M |
| Lithium sulfate | 0.05 M or 0.1 M | 1.0 M, 2.0 M, or 5.0 M | 0.2 M, 0.35 M, 0.5 M |
| Sodium chloride, potassium chloride, ammonium phosphate, sodium phosphate, potassium phosphate, sodium citrate, | 0.01 M, 0.025 M, 0.05 M, 0.1 M | 1.0 M, 1.5 M, 2.0 M, 2.5 M, or 5.0 M | 0.1 M, 0.2 M, 0.35 M, 0.5 M, 0.75 M, 1.0 M, |

-continued

| | Value Ranges; Minimum (selected from below) to Maximum (selected from below) | | |
|---|---|---|---|
| | Minimum Values: | Maximum Values: | Examples of Specific Values: |
| potassium citrate, ammonium acetate, sodium acetate, ammonium sulfate, magnesium sulfate, or sodium sulfate | or 0.5 M | | 1.5 M |
| di-ammonium hydrogen phosphate | 0.1 M, 0.5 M | 1.5 M, 2.0 M | 1.0 M |
| pH buffer conditions: | | | |
| 0.05 M, 0.1 M, or 0.15 M HEPES | pH 4.0, 5.0, or 6.0 | pH 8.0, 8.5, or 9.0 | pH 6.5, 6.75, 6.9, 7.0, 7.25, 7.5, 7.75 |
| 0.05 M, 0.1 M, or 0.15 M Tris-HCl | pH 5.0, 6.0, or 7.0 | pH 9.0, 9.5, or 10.0 | pH 7.25, 7.5, 7.75, 8.0, 8.25, 8.5, 8.75 |
| 0.05 M, 0.1 M, or 0.15 M Bicine | pH 5.0, 6.0, or 7.0 | pH 10.0, 10.5, or 11.0 | pH 8.0, 8.25, 8.5, 8.75, 9.0, 9.25, 9.5 |
| 0.05 M, 0.1 M, or 0.15 M sodium acetate | pH 4.0 | pH 5.0 | pH 4.0, 4.5, 5.0 |
| 0.05 M, 0.1 M , 0.15 M imidazole | pH 7.5 | pH 8.5 | pH 8.0 |
| 0.1 M CAPS (3-[cyclohexylamino]-1-propanesulfonic acid), pH 10.5 | pH 9.0, pH 9.5 | pH 11.5, pH 12.0 | pH 10.0, pH 10.5, pH 11.0 |
| PEG or 2-methyl-2,4-pentanediol (MPD) conditions: | | | |
| Polyethylene glycol (PEG) 200, 300, 400, 600, 750, 900, 1000, 1450, 3350, 4000, 4500, 6000, or 8000 | 0, 1, 2, 3, 5, or 7.5% (liquid: v/v; solid: w/v) | 32, 35, 40, 45, or 50% (liquid: v/v; solid: w/v) | 10, 12, 15, 20, 25, 30% (liquid: v/v; solid: w/v) |
| 2-Methyl-2,4-pentanediol (MPD) | 0, 1, 2, 3, 4, 5, 6, 7, or 8% (v/v) | 40, 45, 50, 60, or 70% (v/v) | 10, 12, 15, 20, 25, 30, 32, 35% (v/v) |
| Metal Ion ("Cofactor") conditions: | | | |
| nickel chloride | 0.001 M or 0.005 M | 0.02 M, 0.05 M, 0.1 M, or 0.2 M | 0.01 M |
| compounds of the following metals: zinc, copper, calcium, manganese, and magnesium | 0.001 M, 0.002 M, or 0.003 M | 0.05 M, 0.1 M, 0.2 M, 0.5 M, 1.0 M, or 2.0 M | 0.005 M, 0.01 M, 0.02 M |

EXAMPLE 4

Testing Properties of Crystalline Polypeptides

After polypeptide crystals are formed, they can be subjected to various analyses to confirm their polypeptide content and to further examine their physical structure. For example, if necessary individual crystals can be removed from the crystallization solution and washed with aqueous or organic solvents or additives, then dried (for example, by air drying, by passing a stream of inert gas over the crystal, by lyophilization, or by vacuum). Crystals can be isolated, removed from the crystal growth drop, and then mounted for X-ray diffraction.

As another example, polypeptide crystals can be removed from crystallization solution and washed or rinsed, or the majority of crystallization solution can be removed from the crystals and replaced with a different solution. In this way, the particular salt that was using in the crystallization procedure can be replaced in the crystal lattice with a different salt. In one embodiment of the invention, crystallized TNFR2 polypeptides such as crystalline etanercept are separated from the crystallization buffer and placed in a solution containing a salt of sodium, potassium, or magnesium (for example, sodium acetate, sodium chloride, sodium citrate, sodium phosphate, sodium sulfate, potassium chloride, potassium citrate, or magnesium sulfate). For X-ray diffraction, the replacement solution can contain heavy atoms useful in determining the atomic coordinates of the crystallized polypeptide. As a further embodiment, TNFR2 polypeptides can be cocrystallized with their ligand, for example etanercept can be cocrystallized with TNF-alpha, for determination of the detailed structure of the TNFR-ligand interaction.

In a further example, polypeptide crystals can be removed from crystallization solution and solubilized in an appropriate buffer for further testing, such as an SDS-containing buffer for analysis of the polypeptide that had been crystallized by gel electrophoresis. Methods for analysis of proteins by gel electrophoresis are well known and include staining a gel with silver or Coomassie blue dye, and comparing the electrophoretic migration of the polypeptide that had been crystallized with the migration of polypeptide markers of known molecular weight. In another method, the polypeptide is visualized in the gel by use of a labeled antibody that specifically binds to the polypeptide. Polypeptides that have been crystallized can also be solubilized in buffers appropriate for amino acid sequencing by Edman degradation, for mass spectrometry, for other spectrographic scattering, refraction, diffraction, or absorption studies, or for labeling of the polypeptide by attachment of a label molecule to the polypeptide.

EXAMPLE 5

Assay of Protein Content of ENBREL® (Etanercent) Crystal

The "hanging-drop" method of crystallization, as described in Example 1 above, was used to prepare additional crystals of etanercept. Each well contained 100 microliters of the crystallization reagent in the reservoir; the crystallization reagent in this experiment was 0.2M ammonium acetate, 0.1M Tris pH 8.5, and 45% 2-methyl-2,4-pentanediol (MPD). Etanercept was placed into a solution containing 25 mM sodium phosphate pH 6.3, 100 mM NaCl, then concentrated to 29-30 mg/mL, for example, to 29.6 mg/mL. Drops were made by adding 1 microliter of this 29 mg/mL solution of etanercept to 1 microliter of the crystallization reagent, for a final etanercept concentration in the drop of approximately 14.5-15 mg/mL. The final concentration of the etanercept in the drop was found to be an important factor in achieving crystallization under these particular crystallization conditions, with a final etanercept concentration of approximately 15 mg/mL being effective for crystallization in repeated experiments, while final concentrations of less than 10 mg/mL or greater than 25 mg/mL were not effective. The drops were allowed to vapor exchange with the reagent in the reservoir for approximately one to three weeks at ambient room temperature (20±3 degrees C.). Crystals, usually as two to four independent nucleations per drop, formed and appeared as multibranched or dendritic structures with numerous projections or branches off of the main structure. The overall dimensions of each intact branch were approximately 50 micrometers in length from the nucleation center, approximately 30 micrometers in width, and approximately 10 micrometers in thickness or depth. One of the branches was removed from the crystal with a nylon loop, washed with the above crystallization reagent in three serial washes, solubilized in 4xSDS Laemmli buffer, and then placed in the well of an SDS-polyacrylamide gel and subjected to electrophoresis. Following the electrophoresis the gel was stained with silver, and there is a clearly visible silver-stained band in the lane run from the crystallized protein that migrated to the same extent as protein from the etanercept preparation used to produce the crystal. This SDS-polyacrylamide gel electrophoresis assay was repeated using other branches from crystals produced in these experiments, and staining of a band of solubilized crystalline material, with the same electrophoretic migration as etanercept, was also achieved using Coomassie Blue stain. Therefore, the crystals that formed from the etanercept solution contain material that is apparently etanercept, because it migrates in an SDS-polyacrylamide gel and produces a protein band in the gel in the same fashion that a known sample of etanercept protein does.

EXAMPLE 6

Testing Biological Activity of Crystallized Polypeptides

As described in the example above, polypeptide crystals can be recovered from the crystallization solution, optionally placed in a different solution, washed, and/or dried to remove crystallization buffer, and then solubilized in an appropriate solution for further assays. The biological activities of TNFR2 polypeptides can be tested using any of a number of assays, for example binding assays to determine the ability of previously crystallized TNFR2 (i.e. reconstituted TNFR2 polypeptide) to bind to its ligand. The following examples illustrate assays for measuring the biological activity of those TNFR2 polypeptides that bind TNF-alpha, such as etanercept (see for example Mohler et al., 1993, J Immunol 151: 1548-1561), but those of skill in the art will recognize that such assays can be modified for use in measuring the biological activities of other TNFR2 polypeptides.

Binding Competition Assay

Labeled human TNF-alpha such as [$^{125}$I]TNF-alpha at 0.5 nM is incubated in binding medium (RPMI 1640, 2.5% BSA, 50 mM HEPES pH 7.4, 0.4% NaN$_3$) for two hours at 4 degrees C. with serially diluted competitive binding agents (for example etanercept reconstituted from crystalline form, or another TNF-alpha-binding TNFR2 polypeptide that has been reconstituted from crystalline form, or unlabeled human TNF-alpha, or uncrystallized etanercept as a control) and 2×10$^6$ U937 cells. Duplicate aliquots are subsequently removed, centrifuged through a phthalate oil mixture to separate free and bound ligand, and the radioactivity (cell-bound [$^{125}$I]TNF-alpha) is measured using a gamma counter. Nonspecific binding values are determined by inclusion of a 200×molar excess of unlabeled TNF-alpha and were subtracted from total binding data to yield specific binding values (see for example Park et al., 1990, *J Exp Med* 171: 1073-1089).

Rescue from LPS-Induced Mortality

Injection of a lethal dose of LPS (lipopolysaccharide) raises serum TNF-alpha levels in mice, causing mortality if a sufficient amount of an agent that neutralizes the effects of TNF-alpha is not also administered (see for example Mohler et al., 1993, *J Immunol* 151: 1548-1561). LPS, such as bacterial LPS derived from *E. coli*, is resuspended at 10 mg/mL in sterile saline and stored at −20 degrees C. in small aliquots. The LPS is diluted to the proper concentration and sonicated for one minute before injection. Mice such as BALB/c female mice (18 to 20 g) are injected intravenously with an LD60 to LD100 dose of LPS (300 to 400 micrograms) in 0.2 mL of saline. The LPS is injected either alone or in conjunction with etanercept reconstituted from crystalline form, or another TNF-alpha-binding TNFR2 polypeptide that has been reconstituted from crystalline form, or control proteins such as uncrystallized etanercept or human IgG. Survival is monitored for at least 5 days. The presence of active reconstituted TNF-alpha-binding TNFR2 polypeptide is indicated by increased survival of LPS-injected mice, when a sufficient amount of the reconstituted TNF-alpha-binding TNFR2 polypeptide is administered.

The present invention has been described in terms of particular embodiments found or proposed to comprise certain modes for the practice of the invention. It will be appreciated by those of ordinary skill in the art that, in light of the present disclosure, numerous modifications and changes can be made in the particular embodiments exemplified without departing from the intended scope of the invention.

| Sequences Presented in the Sequence Listing | | |
|---|---|---|
| SEQ ID NO | Type | Description |
| SEQ ID NO:1 | Amino acid | Human tumor necrosis factor receptor 2; (TNFR2, p75, CD120b, TNFRSF1B); Swiss-Prot Database Accession No. P20333 |

-continued

| Sequences Presented in the Sequence Listing | | |
|---|---|---|
| SEQ ID NO | Type | Description |
| SEQ ID NO:2 | Amino acid | Human immunoglobulin gamma-1 chain constant region (IgG1; Swiss-Prot Database Accession No. P01857) |
| SEQ ID NO:3 | Amino acid | Variant of human immunoglobulin gamma-1 chain constant region (SEQ ID NO: 2 with Asp239->Glu; Leu241->Met) |
| SEQ ID NO:4 | Amino acid | Etanercept |

What is claimed is:

1. A crystal of etanercept in the form of a needle or a rod.

2. A crystal of etanercept as in claim 1, wherein the crystal is in the form of a rod.

3. A crystal of etanercept as in claim 1, wherein the crystal has a maximum length of between 0.5 millimeters and 1.5 millimeters.

4. A crystal of etanercept as in claim 1, wherein the crystal has a maximum length of between 0.05 millimeters and 0.3 millimeters.

5. A crystal of etanercept as in claim 1, wherein the crystal comprises a salt selected from the group consisting of ammonium acetate, ammonium phosphate, ammonium sulfate, di-ammonium hydrogen phosphate, lithium chloride, lithium sulfate, magnesium sulfate, potassium chloride, potassium citrate, potassium phosphate, sodium acetate, sodium chloride, sodium citrate, sodium phosphate, and sodium sulfate.

6. A crystal of etanercept as in claim 1, wherein the crystal comprises ammonium acetate, ammonium phosphate, di-ammonium hydrogen phosphate, and sodium chloride.

7. A method of making a crystal of etanercept, wherein the method comprises combining a solution of etanercept polypeptide with a crystallization buffer comprising a salt.

8. The method of claim 7, wherein the combination is placed in vapor equilibrium with a reservoir of crystallization buffer.

9. The method of claim 7, wherein the crystallization buffer has a pH between 4.0 and 10.5.

10. The method of claim 7, wherein the salt is selected from the group consisting of ammonium acetate, ammonium phosphate, ammonium sulfate, di-ammonium hydrogen phosphate, lithium chloride, lithium sulfate, magnesium sulfate, potassium chloride, potassium citrate, potassium phosphate, sodium acetate, sodium chloride, sodium citrate, sodium phosphate, and sodium sulfate.

11. The method of claim 7, wherein the concentration of salt in the crystallization buffer is between 0.04M and 1.2M.

12. The method of claim 7, wherein the crystallization buffer further includes 2-methyl-2,4-pentanediol (MPD) or polyethylene glycol (PEG).

13. The method of claim 7, further comprising removing at least a portion of the crystallization buffer after crystals have formed.

14. The method of claim 13 wherein the portion of crystallization buffer is removed by centrifugation.

15. The method of claim 13, wherein the crystals are placed in a solution containing an organic additive.

16. The method of claim 13, further comprising the addition of an excipient.

17. The method of claim 16 wherein the excipient is selected from the group consisting of sucrose, trehalose, or sorbitol.

18. The method of claim 15 wherein the organic additive is ethanol or isopropanol.

19. The method of claim 7, further comprising drying crystals that have formed.

20. The method of claim 19 wherein the crystals are dried by exposure to air, or by exposure to a vacuum, or by exposure to nitrogen gas.

21. An etanercept crystal produced by the method of claim 7.

22. A method of making a crystal of etanercept, wherein the method comprises combining a solution of etanercept polypeptide with co-solute means.

23. The method of claim 22 wherein the solution of etanercept polypeptide is further combined with crystallization buffering means.

24. A composition comprising an etanercept crystal of claim 1.

25. A method comprising administering to a subject an effective amount of the crystalline etanercept of claim 1.

26. The method of claim 25 wherein the subject has a condition characterized by excessive TNF-alpha levels.

27. The method of claim 26 wherein the administration of crystalline etanercept reduces levels of TNF-alpha in the serum or tissues of the subject.

28. The method of claim 26 wherein the subject has rheumatoid arthritis, psoriatic arthritis, psoriasis, or ankylosing spondylitis.

29. A composition comprising etanercept in crystalline form and an ingredient selected from the group consisting of: acidifying means, active ingredients, propellant means, aggregation inhibiting means, denaturant means, alkalizing means, anticaking means, antifoaming means, antioxidant means, formulation buffering means, chelating means, coating means, coloring means, complex-forming means, dessicating means, filtering means, flavoring means, moisture-retaining means, ointment means, plasticizing means, carrier means, preserving means, solubilizing means, stabilizing means, means for dissolving, adsorbing means, stiffening means, suppository means, viscosity-increasing means, sweetening means, tablet binding means, diluent means, tablet disintegrant means, lubricating means, tonicity modifying means, vehicle means, water-repelling means, and sustained-release means.

* * * * *